(12) United States Patent
Aydt et al.

(10) Patent No.: US 7,851,501 B2
(45) Date of Patent: Dec. 14, 2010

(54) AROMATIC NITROCATECHOL COMPOUNDS AND THEIR USE FOR MODULATING PROCESSES MEDIATED BY CELL ADHESION MOLECULES

(75) Inventors: Ewald M. Aydt, Berlin (DE); Remo Kranich, Berlin (DE)

(73) Assignee: Revotar Biopharmaceuticals AG, Hennigsdorf (DE)

( * ) Notice: Subject to any disclaimer, the term of this patent is extended or adjusted under 35 U.S.C. 154(b) by 0 days.

(21) Appl. No.: 12/067,341

(22) PCT Filed: Sep. 20, 2006

(86) PCT No.: PCT/EP2006/009155

§ 371 (c)(1),
(2), (4) Date: May 1, 2008

(87) PCT Pub. No.: WO2007/039114

PCT Pub. Date: Apr. 12, 2007

(65) Prior Publication Data

US 2009/0105280 A1    Apr. 23, 2009

(30) Foreign Application Priority Data

Sep. 20, 2005   (EP)   ................... 05020508

(51) Int. Cl.
*A01N 43/06* (2006.01)
(52) U.S. Cl. ............ 514/438; 514/252.1; 514/256; 514/277; 544/242; 546/1
(58) Field of Classification Search ............ 514/438, 514/252.1, 256, 277; 544/242; 546/1
See application file for complete search history.

(56) References Cited

U.S. PATENT DOCUMENTS

| | | | |
|---|---|---|---|
| 4,363,813 A | 12/1982 | Kawasaki et al. | |
| 5,374,772 A | 12/1994 | Casson et al. | |
| 6,248,790 B1 | 6/2001 | Uckun et al. | |
| 6,432,957 B1 | 8/2002 | Kodoma et al. | |
| 2003/0187306 A1 | 10/2003 | Sinha et al. | |
| 2005/0113416 A1 | 5/2005 | Wang et al. | |
| 2008/0249107 A1 | 10/2008 | Kranich et al. | |

FOREIGN PATENT DOCUMENTS

| | | | |
|---|---|---|---|
| EP | 0217204 A1 | 4/1987 |
| EP | 0465122 A1 | 1/1992 |
| EP | 00426468 B1 | 9/1995 |
| EP | 0840606 B1 | 6/2000 |
| EP | 0758243 B1 | 3/2003 |
| EP | 1481669 A1 | 12/2004 |
| EP | 1577289 A1 | 9/2005 |
| EP | 1627644 A1 | 2/2006 |
| JP | 2003 055369 A | 6/2003 |
| WO | WO 97/01569 A1 | 1/1997 |
| WO | WO 99/29705 A2 | 6/1999 |
| WO | WO 99/29705 A3 | 6/1999 |
| WO | WO 99/29706 A2 | 6/1999 |
| WO | WO 99/29706 A3 | 6/1999 |
| WO | WO 00/33836 A1 | 6/2000 |
| WO | WO 97/01335 | 1/2003 |
| WO | WO 03/075905 A1 | 9/2003 |
| WO | WO 03/097658 A2 | 11/2003 |
| WO | WO 03/097658 A3 | 11/2003 |
| WO | WO 2004/018502 A1 | 3/2004 |

OTHER PUBLICATIONS

R.P. McEver, "8 Interactions of Selectins with PSGL-1 and Other Ligands", *Ernst Schering Res. Found. Workshop*, 2004, 44, pp. 137-147.

(Continued)

*Primary Examiner*—Kamal A Saeed
*Assistant Examiner*—Valerie Rodriguez-Garcia
(74) *Attorney, Agent, or Firm*—J. A. Lindeman & Co., PLLC

(57) ABSTRACT

Pharmaceutical compositions comprising at least one compound of e.g. the formulas (Ie) and a pharmaceutically acceptable carrier which is useful in a medicine

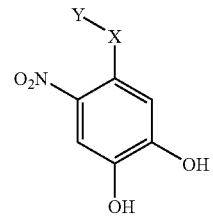

wherein the symbols and substituents have the following meaning
—X— is e.g.

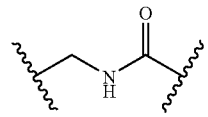

and Y is e.g.

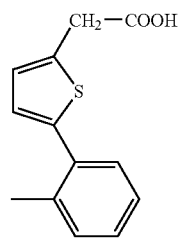

or the pharmaceutically acceptable salts, esters or amides and prodrugs of the above identified compounds can be applied to modulate the in-vitro and in-vivo binding processes mediated by E-, P- or L-selectin binding.

12 Claims, No Drawings

OTHER PUBLICATIONS

G. Constantin, "PSGL-1 as a Novel Therapeutic Target", Drug News Perspect 17(9), Nov. 2004, pp. 579-586.

Okazaki et al., "Enhancement of Metastatic Activity of Colon Cancer as influenced by Expression of Cell Surface Antigens", Journal of Surgical Research, 78, JR985298, pp. 78-84, Sep. 22, 1997.

A.M. Müller et al., "Heterogeneous expression of cell adhesion molecules by endothelial cells in ARDS", Journal of Pathology, 2002, 198(2), pp. 270-275.

R.P. McEver, "Selectin-carbohydrate interactions during inflammation and metastasis", Glycoconjugate Journal (1997) 14: 585-591, pp. 585-591.

R.P. McEver et al., "Perspectives Series: Cell Adhesion in Vascular Biology" "Role of PSGL-1 Binding to Selectins in Leukocyte Recruitment", J. Clin. Invest., The American Society for Clinical Investigation, Inc., vol. 100, No. 3, Aug. 1997, pp. 485-492.

A. Di Stefano et al., "Upregulation of Adhesion Molecules in the Bronchial Mucosa of Subjects with Chronic Obstructive Bronchitis", Am. J. Respir. Crit. Care. Med., 1994, vol. 149, No. 3, pp. 803-810.

S. Terajima et al., "An important role of tumor necrosis factor-$\alpha$ in the induction of adhesion molecules in psoriasis", Arch. Dermatol. Res., 1998, 290, pp. 246-252.

M. Sperandio et al., "Blocking Leukocyte Rolling: Does it have a Role in Disease Prevention?", Vascular Disease Prevention, 2004, 1, pp. 185-195.

C.A. Lipinski et al., "Experimental and computational approaches to estimate solubility and permeability in drug discovery and development settings", Advanced Drug Delivery Reviews, 23, 1997, pp. 3-25.

H. Ulbrich et al., "Leukocyte and endothelial cell adhesion molecules as targets for therapeutic interventions in inflammatory disease", Trends in Pharmacological Sciences, 2003, 24(12), pp. 640-647.

S.J. Romano, "Selectin Antagonists, Therapeutic Potential in Asthma and COPD", Treat. Respir. Med. 2005, 4(2), pp. 85-94.

M.P. Schön, "Inhibitors of selectin functions in the treatment of inflammatory skin disorders", Therapeutics and Clinical Risk Management, 2005, 1(3), pp. 201-208.

M. Kumamoto et al., "Effects of pH and Metal Ions on Antioxidative Activities of Catechins", Biosci. Biotechnol. Biochem., 64 (1), 2001, pp. 126-132.

E. Sergediene et al., "Prooxidant toxicity of polyphenolic antioxidants to HL-60 cells: description of quantitative structure-activity relationships", FEBS Lettes 462 (1999) 392-396.

K. Satoh et al., "Copper, but not Iron, Enhances Apoptosis-Inducing Activity of Antioxidants", Anticancer Research 17: (1997), pp. 2487-2490.

N. Sakuguchi et al., "Reactive Oxygen Species and Intracellular $Ca^{2+}$, Common Signals for Apoptosis Induced by Gallic Acid", Biochemical Pharmacology, vol. 55, pp. 1973-1981, 1998.

D. Bock et al., Innovative Strategy in Inflammatory Diseases, New Drugs, 2003, D04, 28, pp. 28-30.

E. Aydt et al., "Development of Synthetic Pan-Selectin Antagonists: A New Treatment Strategy for Chronic Inflammation in Asthma", Pathobiology, 2002-2003, 70, pp. 297-301.

N.V. Bovin, "Neoglycoconjugates: trade and art", Biochem. Soc. Symp., 2002, (69), pp. 143-160.

N.V. Bovin, "Polyacrylamide-based blycoconjugates as tools in glycobiology", Glycoconjugate Journal 15, 1998, pp. 431-446.

T.V. Pochechueva et al., "P-Selectin Blocking Potency of Multimeric Tyrosine Sulfates In Vtiro and In Vivo", Bioorganic & Medicinal Chemistry Letters 13(10), 2003, pp. 1709-1712.

G. Weitz-Schmidt et al., "An E-Selectin Binding Assay Based on a Polyacrylamide-Type Glycoconjugate", Analytical Biochemistry 238, 1996, pp. 184-190.

C.C.M. Appledoorn et al., "Rational Optimization of a Short Human P-selectin-binding Peptide Leads to Nanomolar Affinity Antagonists", Journal of Biological Chemistry, vol. 278, No. 12, Mar. 21, 2003, pp. 10201-10207, XP002275710.

R. Yamazaki et al., "Diarylheptanoids suppress expression of leukocyte adhesion molecules on human vascular endothelial cells", European Journal of Pharmacology, vol. 404, No. 3, Sep. 22, 2000, pp. 375-385, XP009062460.

C.C.M. Appledoorn et al., "Gallic Acid Antagonizes P-Selectin-Mediated Platelet-Leukocyte Interactions, Implications for the French Paradox", *Circulation* Jan. 4/11, 2005, 111, pp. 106-112.

N. Kaila et al., "Quinic Acid Derivatives as Sialyl Lewis$^x$-Mimicking Selectin Inhibitors: Design, Synthesis, and Crystal Structure in Complex with E-Selectin", J. Med. Chem. 2005, 48, pp. 4346-4357.

D.H. Slee et al., "Development of Potent Non-Carbohydrate Imidazole-Based Small Molecule Selectin Inhibitors with Antiinflammatory Activity", J. Med. Chem. 2001, 44, pp. 2094-2107.

P.T. Mannisto et al., "Catechol-*O*-methyltransferase (COMT): Biochemistry, Molecular Biology, Pharmacology, and Clinical Efficacy of the New Selective COMT Inhibitors", Pharmacological Reviews, The American Society for Pharmacology and Experimental Therapeutics, 1999, vol. 51, No. 4, pp. 593-628.

J. Axelrod et al., "Enzymatic O-Methylation of Epinephrine and Other Catechols", J. Biol. Chem., 1958, 223(3), pp. 702-705.

N. Haramaki et al., "Role of Ascorbate in Protection by Nitecapone Against Cardiac Ischemia-Reperfusion Injury", Biochemical Pharmacology, vol. 50, No. 6, pp. 839-843, 1995.

E. Nissinen et al., "The COMT inhibitor, entacapone, reduces levedopa-induced elevations in plasma homocysteine in healthy adult rats", J. Neural. Transm., 2005, 112, pp. 1213-1221.

Y.J. Suzuki et al., "Antioxidant Properties of Nitecapone (OR-462)", Free Radical Biology & Medicine, 1992, vol. 13, pp. 517-525.

L. Marcocci et al., "Nitecapone: A Nitric Oxide Radical Scaventer", vol. 34, No. 3, Oct. 1994, Biochemistry and Molecular Biology International, pp. 531-541.

T. Helkamaa et al., "Entacapone protects from angiotensin II-induced inflammation and renal injury", Journal of Hypertension, 2003, 21, pp. 2353-2363.

M. Friedrich et al., "Pan-selectin antagonism improves psoriasis manifestation in mice and man", Arch Dermatol Res., 2006, vol. 297: pp. 345-351, XP002370636.

Van De Waterbeemd H et al., "Property-Based Design: Optimization of Drug Absorption and Pharmacokinetics," J. Med. Chem. 44(9):1313-1333 (2001).

Nov. 18, 2009, Office Action in U.S. Appl. No. 12/067,059.

Nov. 16, 2009, Office Action in U.S. Appl. No. 12/067,389.

AROMATIC NITROCATECHOL COMPOUNDS AND THEIR USE FOR MODULATING PROCESSES MEDIATED BY CELL ADHESION MOLECULES

The present invention relates to compounds, compositions and methods for modulating the in vitro and in vivo processes mediated by cell adhesion molecules. The disclosed small molecules are aromatic nitro compounds which modulate cell adhesion molecule-mediated functions potently.

Cell-adhesion molecule-mediated functions are part of a complex cascade leading to the migration of circulating white blood cells (leukocytes) from the blood stream into the surrounding tissue (transmigration). Physiologically, leukocyte transmigration is of critical importance for homeostasis and immuno-surveillance of living beings including humans. Lymphocytes for example, are constitutively leaving the blood stream into lymphatic tissues in order to patrol for harmful antigens. Under pathological circumstances however, e.g. local or systemic inflammation and/or injury of the vascular system, this fundamental process is dys-regulated, at least in part, due to an increased surface expression of E- and P-selectin. Consequently, the excessive leukocyte transmigration leads to a pathological cellular infiltrate with subsequent tissue damage in several clinically relevant settings. Disease states such as Acute Lung Injury (ALI), Acute Respiratory Distress Syndrome (ARDS), Asthma bronchiale (asthma), Chronic Obstructive Pulmonary Disease (COPD), Psoriasis, Rheumatoid Arthritis, and Sepsis are all associated with tissue inflammation induced and perpetuated by pathologically activated leukocytes infiltrating the respective tissue. In addition, exaggerated leukocyte infiltration contributes to the pathogenesis of Ischemic-Reperfusion Injury (IRI) associated with organ transplantation, cardiopulmonary bypass or percutaneous transluminal angioplasty.

To transmigrate, leukocytes must bind to the wall of the vascular endothelium to diffuse through the cell wall of the capillary into the surrounding tissue. Therefore, leukocytes have to roll onto and then adhere to the endothelial cell wall (initial rolling or "tethering"). This primary event in transmigration is mediated by the selectin family of cell-adhesion molecules. In addition to directly binding to the endothelium, leukocytes can adhere to other leukocytes, leukocyte-particles, platelets or platelet-derived particles that are already attached to the endothelium.

The selectin family of adhesion molecules is comprised of three structurally related calcium-dependent carbohydrate binding cell surface proteins, E-, P- and L-selectin. E-selectin is expressed only on inflamed endothelium, P-selectin is expressed on inflamed endothelium as well as on platelets and L-selectin is expressed on leukocytes. Selectins are composed of an amino terminal lectin domain, an epidermal growth factor (EGF)-like domain, a variable number of complement receptor-related repeats, a hydrophobic transmembrane domain and a C-terminal cytoplasmic domain. The binding interactions leading to the adhesion of the leukocytes are supposed to be mediated by contact of the lectin domain of the selectins and various carbohydrate ligands on the surface of the leukocytes.

All three selectins can bind with low affinity to the carbohydrate sialyl Lewis$^x$ (sLe$^x$), a glycosyl moiety present on the surface of most leukocytes. A structurally related glycosyl moiety, sialyl Lewis$^a$ (sLe$^a$), is predominantly found on the surface of cancer cells [K. Okazaki et al., *J. Surg. Res.*, 1998, 78(1). 78-84; R. P. McEver et al., *Glycoconjugate Journal*, 1997, 14(5), 585-591]. In case of P-selectin, a distinct high affinity glycoprotein ligand has been described [R. P. McEver, R. D. Cummings, *J. Clin. Invest.*, 1997, 100, 485-492], the so-called P-selectin glycoprotein ligand-1 (PSGL-1), which contributes to a high affinity selectin binding by its sLe$^x$ moiety as well as by parts of its peptide components, in particular sulphated tyrosine residues [R. P. McEver, *Ernst Schering Res. Found Workshop*, 2004, 44, 137-147]. PSGL-1 is one of the most important selectin ligands binding with highest affinity to P-selectin, but it also binds to E- and L-selectin [G. Constantin; *Drug News Perspect;* 2004; 17(9); 579-586]. It is a homodimeric sialomucin predominantly expressed on leukocytes.

In inflammatory diseases, dys-regulated transmigration is, at least in part, mediated due to an increased cell surface expression of E- and P-selectin. In contrast to their low basal expression, E- and P-selectin expression is upregulated during inflammation, leading to a substantial recruitment of leukocytes into the inflamed tissue. Although selectin-mediated cell adhesion is required for fighting infection, there are various situations in which such cell adhesion is undesirable or excessive, resulting in severe tissue damage instead of repair. In the case of many acute as well as chronic inflammatory disorders [e.g., asthma, chronic obstructive pulmonary disease (COPD), psoriasis, etc.], an association between infiltration of activated leukocytes into the tissue simultaneously with a marked elevation of tissue expression of corresponding adhesion molecules, particularly E- and P-selectin, has been demonstrated [Muller et al., *J. Pathol.*, 2002, 198(2), 270-275; Di Stefano et al., *Am. J. Respir. Crit. Care. Med.*, 1994, 149(3) 803-810; Terajima et al., *Arch. Dermatol. Res.*, 1998, 290, 246-252]

Leukocyte infiltration may also play a role in inflammatory symptoms in the course of transplant and graft rejection. Also the process of blood clotting is further promoted by leukocyte-leukocyte and leukocyte-platelet binding, which occurs because leukocytes possess both L-selectin and its corresponding ligand PSGL-1 and can thus interact with themselves via PSGL-1, and they can also bind to platelets which carry P-selectin.

Therefore, the modulation of selectin-mediated cell adhesion and other selectin mediated functions, e.g. leukocyte activation, offers a promising possibility to interfere with and stop the inflammation cascade at a very early step. Small molecule selectin antagonists should modulate all three selectins simultaneously as pan-selectin-antagonists to circumvent possible redundancies between the selectins [M. Sperandio et al., *Vascular Disease Prevention*, 2004, 1, 185-195].

Besides sLe$^x$/sLe$^a$, the natural, high affinity ligand PSGL-1 is another template structure for the design of small molecule selectin antagonists. As compared to sLe$^x$/sLe$^a$, PSGL-1 shows high affinity for all three selectins. To find and to detect novel small molecule drugs that compete with PSGL-1 and PSGL-1-like ligands for selectin binding is therefore a promising strategy to develop a novel class of effective pan-selectin antagonists for treating inflammatory disorders. Selectin antagonists may be designed using selectins as well as using a ligand like PSGL-1 as a template structure, since they are intended to modulate the binding between selectins and PSGL-1 or other ligands with similar binding motifs.

Novel small molecule selectin antagonists could meet certain requirements to be drug-like and to have potential oral bioavailability. The term drug likeness is described in the literature [Lipinski; *Adv. Drug Dev. Rev.*, 1997, 23, 3-25]. Beside other molecular properties, passively transported molecules are supposed to have on average a relative molecular weight of less than 500 in order to be drug like. According to these rules it is common to define compounds with a relative molecular weight of less 500 or closely above that as small molecules. Compounds with relative molecular weights above 500 are unlikely to be orally bioavailable. Also the presence of highly polar carbohydrate moieties or a peptidic components is not in accordance with the concept of drug likeness [H. Ulbrich et al., *Trends Pharmacol. Sci.*, 2003, 24(12), 640-647; D. Slee et al., *J. Med. Chem.*, 2001, 44, 2094-2107]. The same accounts for the development of antibody-based drugs, because they are polypeptides and so oral administration is a problem. Moreover, the desired compounds must be stable during the passage through the gastrointestinal tract so that they can be ingested/absorbed latest by the cells of the small intestines. This is not the case for most glycosidic molecules and peptidic structures.

Some nitrocatechols have been developed for the treatment of Morbus Parkinson acting as specific catechol-O-methyl transferase (COMT) inhibitors [J. Axelrod et al., *J. Biol. Chem.* 1958, 233(3), 702-705; P. T. Männisto et al., *Pharmacological Reviews* 1999, 51, 593-628], such as tolcapone, nitecapone, and entacapone [EP00426468]. Nitrocatechols have also been described to have cardioprotective function caused by iron-chelating [N. Haramaki et al., *Biochemical Pharmacology* 1995, 50, 839-843] or decreasing plasma homocysteine levels [E. Nissinen et al., *J. Neural Transm.* 2005, 112, 1213-1221]. Nitecapone has also been reported to act as radical scavenger [Y. J. Suzuki et al., *Free Radical Biology & Medicine*, 1992, 13, 517-525; L. Marcocci et al., *Biochemistry and Molecular Biology International*, 1994, 34, 531-541]. Some observations indicate that entacapone may protect from angiotensin II-induced renal damage [T. Helkamaa et al., *J. Hypertens.*, 2003, 21, 2353-2363].

However, up to date nitrochatechols have not been described as selectin modulating compounds. There have been various investigations to develop low-molecular weight compounds with a modulatory effect on selectin mediated processes. These compounds include disalicylates and disalicylate-based C-glycosides [WO 99/29706], benzyl amino sulfonic acids [WO 03/097658], diglycosylated 1,2-diols [WO 97/01569], substituted 5-membered heterocycles [WO 00/33836], mannopyranosyloxy-phenyl-benzoic acids [EP0758243 B1], piperazine based compounds [U.S. Pat. No. 6,432,957B1], gallic acid derivatives of peptides [WO 2004/018502], gallic acid [C. C. M. Appeldoorn et al., *Circulation* 2005, 111, 106-112; EP 1481669A1], and quinic acid derivatives [N. Kaila et al., *J. Med. Chem.* 2005, 48, 4346-4357].

However, none of these selectin-antagonizing compounds have successfully passed clinical trials up to date [S. J. Romano, *Treat. Respir Med* 2005, 4(2), 85-94; M. P. Schön, *Therapeutics and Clinical Risk Management*, 2005, 1(3), 201-208]. This is due to the fact, that many of these structures have been designed on the basis of the low potency template sLe$^x$. Therefore, sLe$^x$-mimicking structures are likely to show low potency. Other compounds show specificity against different members of the selectin family, but antagonizing only selected selectins can be bypassed by other selectins [M. P. Schön, *Therapeutics and Clinical Risk Management*, 2005, 1(3), 201-208].

In addition, most of the compounds developed so far have high molecular weights and often bear carbohydrates and/or peptides making them prone to degradation and modification by peptidases and/or glycosidases. Carbohydrate-bearing structures have further disadvantages such as high degree of chirality, anomericity, and low probability of transport through lipid bilayers. Similar disadvantages are known for peptide-bearing compounds. Some other compounds developed for antagonizing selectin mediated processes contain pyrogallol-substructures. These motifs are prone to oxidation processes [Kumamoto M. et al., *Biosci. Biotechnol. Biochem.*, 2001, 65(1), 126-132] making the pharmaceutical development of these compounds difficult. In addition, compounds with pyrogallol substructures, such as gallic acid, are known to be cytotoxic [E. Sergediene et al., *FEBS Letters*, 1999, 462, 392-396] and induce apoptosis [K. Satoh et al., *Anticancer Research*, 1997, 17, 2487-2490; N. Sakaguchi et al., *Biochemical Pharmacology*, 1998, 55, 1973-1981].

The leading compound in the field of selectin antagonists is bimosiamose [S. J. Romano, *Treat. Respir Med* 2005, 4(2), 85-94]. Presently bimosiamose [D. Bock et al., New Drugs, 2003, D04, 28, p. 28; EP 0 840 606 B1] is the most advanced compound in clinical studies Recent investigations support the hypothesis that bimosiamose can be considered as PSGL-1 mimetic [E. Aydt, G. Wolff; *Pathobiology;* 2002-2003; 70; 297-301]. This distinguishes bimosiamose from other selectin antagonists. It is, however, a high molecular weight compound with carbohydrate structures. The pan-selectin antagonist bimosiamose seems to lack oral bioavailability. Some observations indicate that bimosiamose shows good affinity for P-selectin and a moderate affinity for E- and L-selectin.

There is a strong medical need for novel highly potent pan-selectin antagonists which modulate selectin-mediated function, e.g. of selectin-dependent cell adhesion, and for the development of methods employing such compounds to modulate conditions associated with selectin-ligand interaction. Most of the available anti-inflammatory pharmaceutical therapies, which are available on the market, comprise mostly corticosteroids or NSAIDs (non steroidal anti-inflammatory drugs) having several serious drawbacks/side effects, and target different steps of the inflammatory cascade. Unlike this, modulating the selectin function is a therapeutic concept intervening the inflammation cascade at a very early stage. Almost all promising selectin antagonists so far failed to become marketed drugs, mostly because of low potency and/or high molecular weight that causes problems in their absorption-distribution-metabolism-excretion (ADME) behaviour and thus in oral bioavailability required for the treatment of most inflammatory disorders like rheumatoid arthritis, septic shock, atherosclerosis, reperfusion injury and many others.

EP-A 1 577 289 discloses aromatic compounds which are hydroxylated in the phenyl part of the molecule and which can be used for the treatment of inflammatory disorders.

In WO 1997/01335 aromatic compounds which are linked to a carbohydrate unit are described. The compounds disclosed by this document are selectin-inhibitors and can be used as therapeutic agents, however, they are structurally different from the nitro-substituted aromatic compounds according to this invention.

In BP-A 1 481 669 polyhydroxy phenols are described which have P-selectin modulating activities.

It is one object of the invention to provide novel small molecules, especially non-glycosylated/non-glycosidic and non-peptidic compounds, which are able to potently antagonize selectin-mediated processes and which have less negative side effects during their application than prior art compounds.

Unlike most of the sLe$^x$-mimicking compounds developed in this field, the inventive compounds are not prone to glycosidases or peptidases. Most of the selectin antagonists developed so far are structurally and biologically based on the properties of sLe$^x$ or sLe$^a$. These resulting compounds showed, therefore, low biological activity like their template structures. This invention, however, provides novel potent small and drug like pan-selectin antagonists that have been invented on the basis of biological in vitro assays mimicking PSGL-1 and PSGL-1-like ligands or any ligands bearing sLe$^x$ or sLe$^a$ and tyrosinesulfate motifs [N. V. Bovin; *Biochem Soc Symp.;* 2002; (69): 143-60. N. V. Bovin; *Glycoconj. J;* 1998; 15(5); 431-46. T. V. Pochechueva et al.; *Bioorg Med Chem Lett.;* 2003; 13(10); 1709-12. G. Weitz-Schmidt et al.; *Anal. Biochem.;* 1996; 23 8; 184-190].

The present invention provides pharmaceutical compositions comprising at least one compound having the general structure of formulas (Ia) or (Ib) or (Ic) or (Id) or (Ie) or (If) and a pharmaceutically acceptable carrier which is useful in medicine,

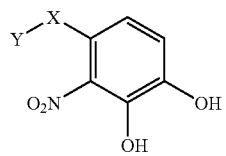
Ia

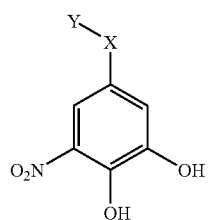
Ib

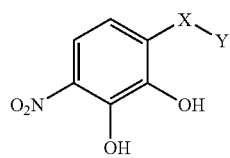
Ic

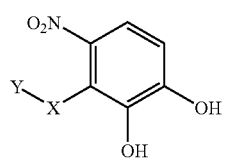
Id

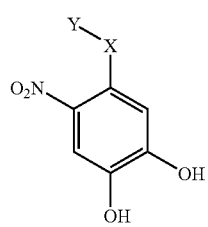
Ie

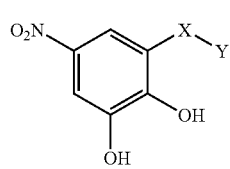
If wherein the symbols and substituents have the following meaning

—X—=

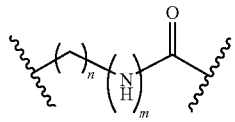
(a)

with m=0, 1; n=an integer from 1 to 3

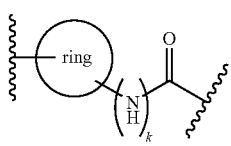
(b)

wherein "ring" is

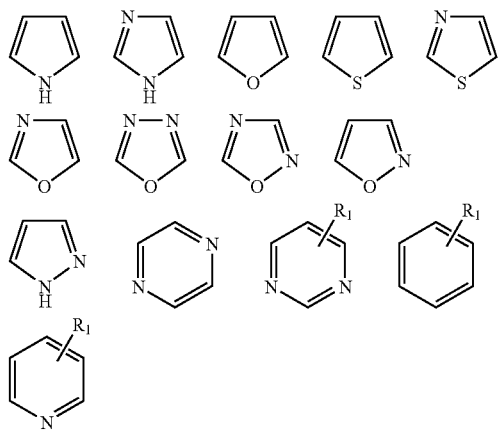

and with $R^1$ being H, $NO_2$, $CF_3$, F, Cl, Br, I, CN, $CH_3$, $NH_2$ NHAlkyl, NHAryl, NHAcyl and k=0, 1

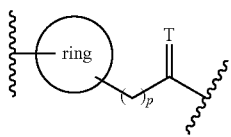
(c)

T being O, S or [H,H]; p=0, 1, 2,

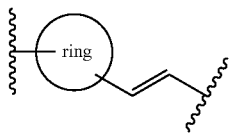
(d)

the double bond is either E- or Z-configurated (e)

[Structure: benzyl-carbonyl group with R¹ substituent]

(f)

[Structure: amide-phenyl-amide with R¹, -E- linker, (NH)ₘ]

[Structure: amide-NH-CH₂-phenyl-amide with R¹, (NH)ₘ]

[Structure: amide-NH-phenyl-CH₂-(HN)ₘ-carbonyl with R¹]

with -E- being —(CH₂—)$_q$NH— and q=0, 1, 2, 3

—Y=

(a)

[Structure with R³, R⁴, R⁵, W—R², (HN)$_s$]

with s being 0 or 1,

R² being CO₂H, CO₂Alkyl, CO₂Aryl, CO₂NH₂, CO₂Aralkyl, SO₃H, SO₂NH₂, PO(OH)₂, 1-H-tetrazolyl-, CHO, COCH₃, CH₂OH, NH₂, NHAlkyl, N(Alkyl)Alkyl', OCH₃, CH₂OCH₃, SH, F, Cl, Br, I, CH₃, CH₂CH₃, CN, CF₃

R³ independently from R² being H, CH₃, CH₂CH₃, CF₃, F, Cl, Br, I, CN, NO₂ and

R⁴ independently from R² and R³ being H, CH₃, CH₂CH₃, CF₃, F, Cl, Br, I, CN, NO₂, R²

R⁵ being H, NO₂, CF₃, F, Cl, Br, I, CN, CH₃, OCH₃, SH, NH₂ and —W—=(CH₂—)$_v$, cis-CH=CH— or trans-CH=CH—, and v being 0, 1, 2;

in case that —W— is cis-CH=CH— or trans-CH=CH—, R² must not be NH₂ or SH;

(b)

[Pyridine structure with W—R², R⁶, (HN)$_s$]

R⁶ independently from R² being H, F, Cl, Me, tert-Bu, CN, NH₂

(c)

[Pyrimidine structure with R⁶, W—R², (HN)$_s$]

(d)

[Piperazine-CH₂-R² structure] [Piperazine-pyrimidine structure]

[Piperazine-pyridine structure with R⁶]

(e)

[Structure with R⁵, Z, (NH)$_s$, (CH₂)$_t$, phenyl]

with t being 0, 1, 2

(f)

[Pyridine structure with R⁶, Z, (NH)$_s$, (CH₂)$_t$]

(g)

[Pyrimidine structure with R⁶, Z, (NH)$_s$, (CH₂)$_t$]

-Z =

(i)

[Phenyl structure with R⁷, W—R²]

R[7] independently from R[2] being H, NO$_2$, CF$_3$, F, Cl, Br, I, CN, CH$_3$, OCH$_3$, SH, NH$_2$, (ii)
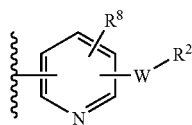

R[8] independently from R[2] being H, F, Cl, Me, tert-Bu, CN, NH$_2$ (iii)
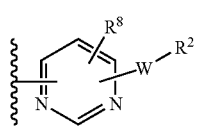

(iv)
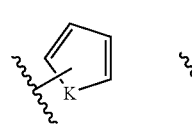

with K=NH, NMe, O, S (v)
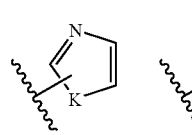

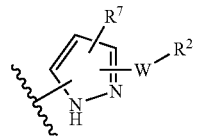

(vi)
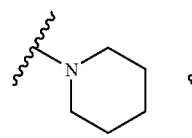

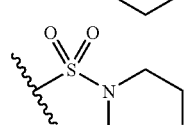

(vii)
—W—R[2]

or the pharmaceutically acceptable salts, esters or amides and prodrugs of the above identified compounds of formulas (Ia), (Ib), (Ic), (Id), (Ie), or (If).

In a preferred embodiment of the invention, the composition comprises at least one compound of the formulas (Ib) or (Ic) or (Ie) or (If) and a pharmaceutically acceptable carrier.

(Ib)
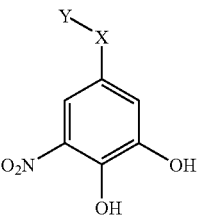

(Ic)
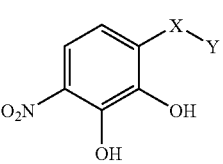

(Ie)
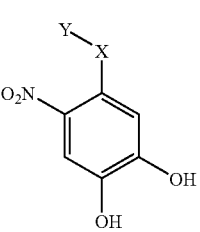

(If)
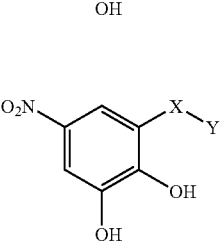

wherein the symbols and substituents have the following meaning

—X—=

(a)
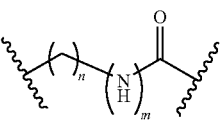

with m=0, 1; n=an integer from 1 to 3

(b)
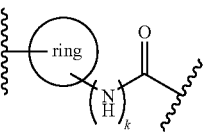

wherein "ring" is

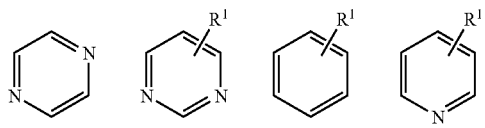

and with $R^1$ being H, $NO_2$, $CF_3$, F, Cl, Br, I, CN, $CH_3$, $NH_2$, NHAlkyl, NHAryl, NHAcyl and k=0, 1, (e)
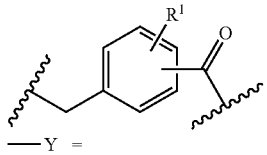

—Y =

(a)
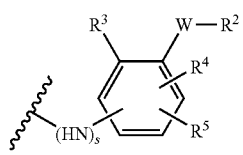

with s being 0 or 1, $R^2$ being $CO_2H$, $CO_2Alkyl$, $CO_2Aryl$, $CO_2NH_2$, $CO_2Aralkyl$, $SO_3H$, $SO_2NH_2$, $PO(OH)_2$, 1-H-tetrazolyl-, CHO, $COCH_3$, $CH_2OH$, $NH_2$, NHAlkyl, N(Alkyl)Alkyl', $OCH_3$, $CH_2OCH_3$, SH, F, Cl, Br, I, $CH_3$, $CH_2CH_3$, CN, $CF_3$ $R^3$ independently from $R^2$ being H, $CH_3$, $CH_2CH_3$, $CF_3$, F, Cl, Br, I, CN, $NO_2$ and $R^4$ independently from $R^2$ and $R^3$ being H, $CH_3$, $CH_2CH_3$, $CF_3$, F, Cl, Br, I, CN, $NO_2$, $R^2$ $R^5$ being H, $NO_2$, $CF_3$, F, Cl, Br, I, CN, $CH_3$, $OCH_3$, SH, $NH_2$ and —W—=—$(CH_2—)_v$, cis-CH=CH— or trans-CH=CH—, and v being 0, 1, 2;

in case that —W— is cis-CH=CH— or trans-CH=CH—, $R^2$ must not be $NH_2$ or SH;

(e)
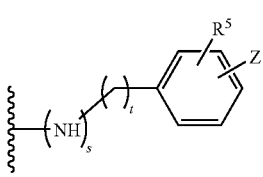

with t being 0, 1, 2

(f)
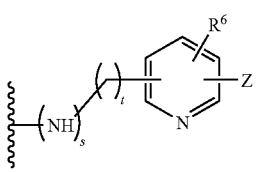

-continued (g)
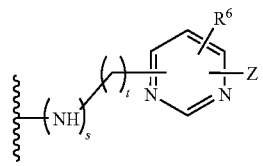

—Z =

(i)
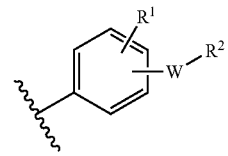

$R^7$ independently from $R^2$ being H, $NO_2$, $CF_3$, F, Cl, Br, I, CN, $CH_3$, $OCH_3$, SH, $NH_2$, (iv)

with K=NH, NMe, O, S (v)
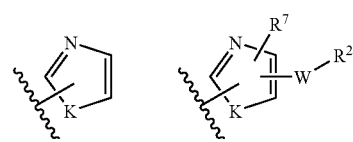

or the pharmaceutically acceptable salts, esters or amides and prodrugs of the above identified compounds of formula (Ib) or (Ic) or (Ie) or (If).

Preferred pharmaceutical compositions comprise compounds of formulas (IIa) or (IIb) or (IIc) or (IId) or (IIe) or (IIf).

IIa
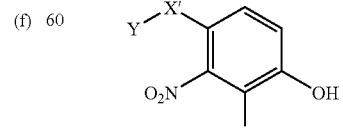

-continued

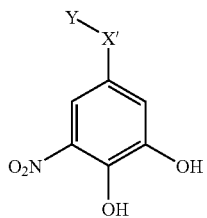
IIb

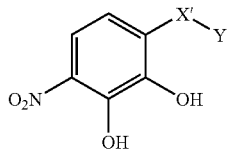
IIc

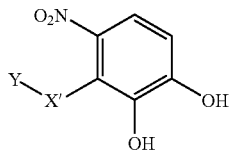
IId

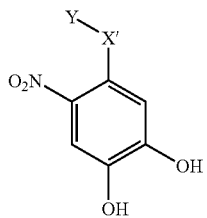
IIe

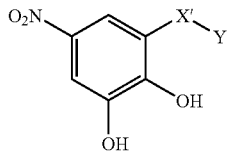
IIf wherein —Y is like defined above and wherein —X'— is X (a), X (b), X (c), and X (d) like defined above.

In a further embodiment, the invention relates to compositions comprising compounds of the structures:

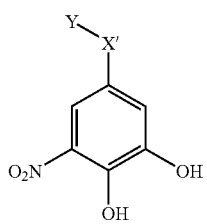
IIb

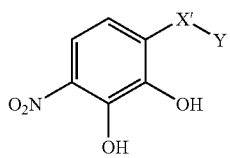
IIc

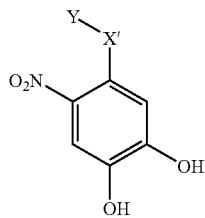
IIe

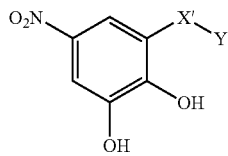
IIf wherein —Y and —X'— as X (a) and X (b) is as defined as above.

Further preferred pharmaceutical compositions comprise compounds of formulas (A1) or (A2) or (A3) or (A4) or (A5) or (A6) or (B11) or (B2) or (B3) or (B4) or (B5) or (B6).

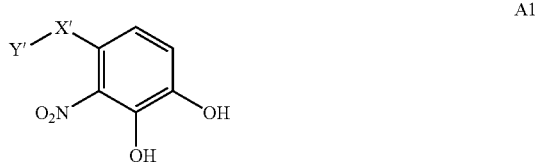
A1

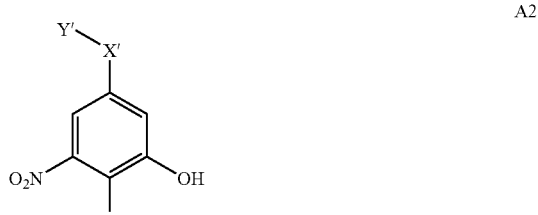
A2

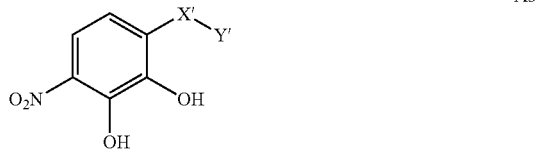
A3

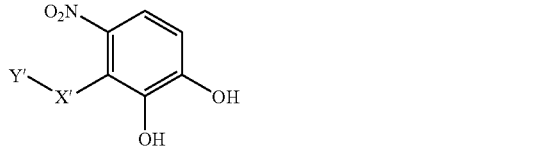
A4

A5

-continued
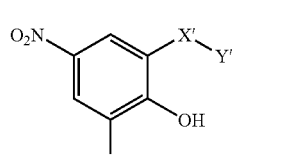
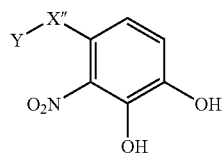
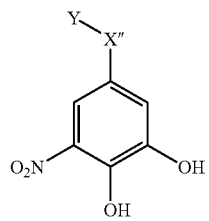
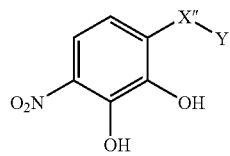
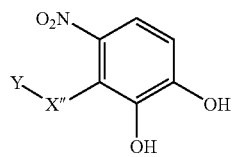
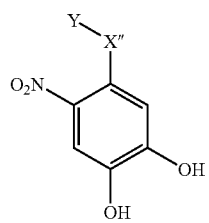
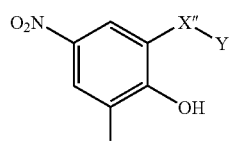
wherein —X'— and —Y are like defined above and wherein —X"— is
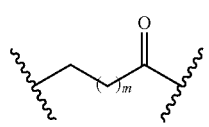 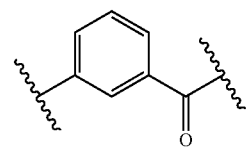
-continued
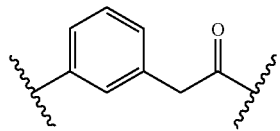 A6
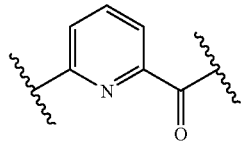 B1
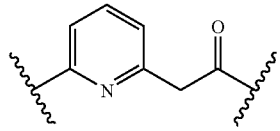 B2
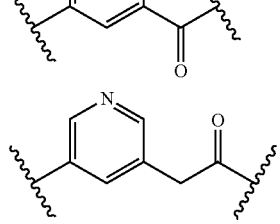 B3
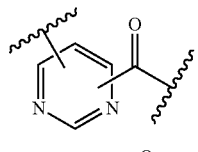
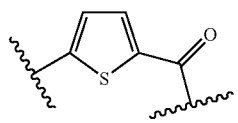 B4
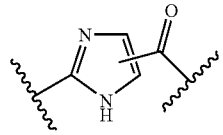
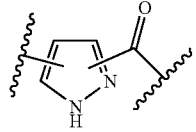 B5
m = 0, 1
and wherein —Y' is
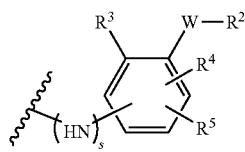 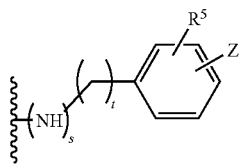
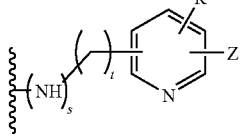 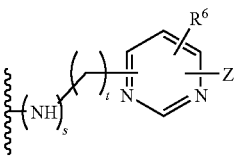
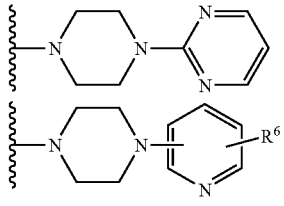
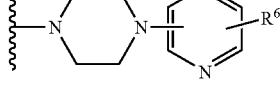

wherein all indices, symbols and substituents are like defined above

In a further embodiment, the invention relates to pharmaceutical compositions comprising compounds of the formula:

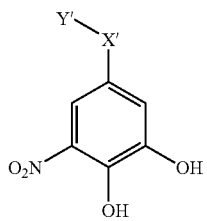
A2

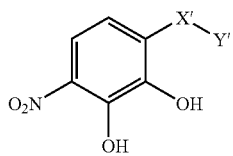
A3

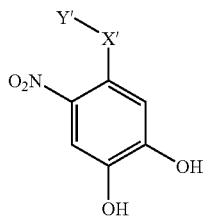
A5

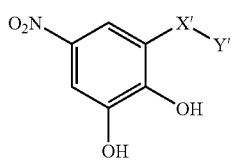
A6

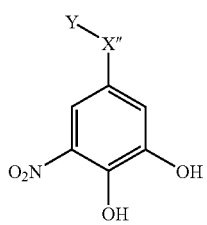
B2

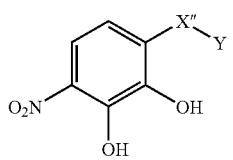
B3

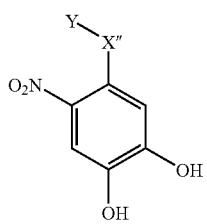
B5

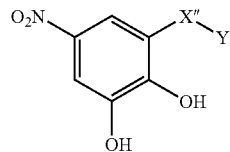
B6 wherein —X'— and —Y are as defined as above and wherein —X"— is

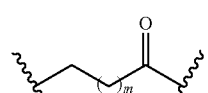
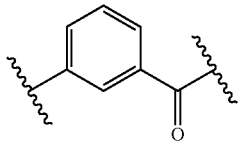
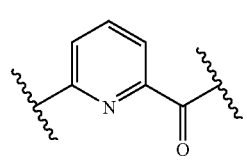
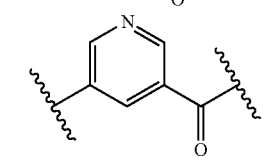
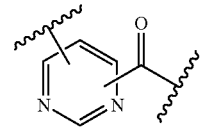

m = 0, 1 and wherein —Y' is

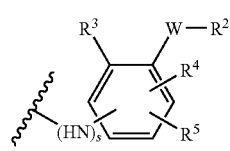
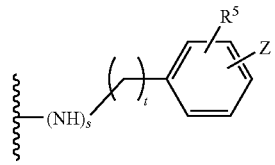

wherein all indices, symbols and substituents are as defined above.

Particularly preferred pharmaceutical compositions comprise compounds of formulas (C1) or (C2) or (C3) or (C4) or (C5) or (C6).

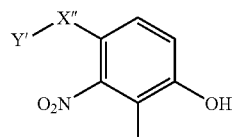
C1

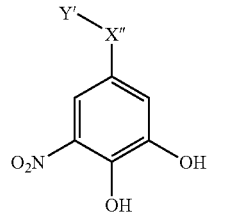
C2 wherein —X"— and —Y' are as defined as above.

Very particularly preferred pharmaceutical compositions comprise compounds of formulas (D1) or (D2) or (D3) or (D4) or (D5) or (D6).

wherein —X"— and —Y' are like defined above.

A further preferred group of compounds of the following composition have the following structures:

wherein —X"— is like defined above and —Y" is

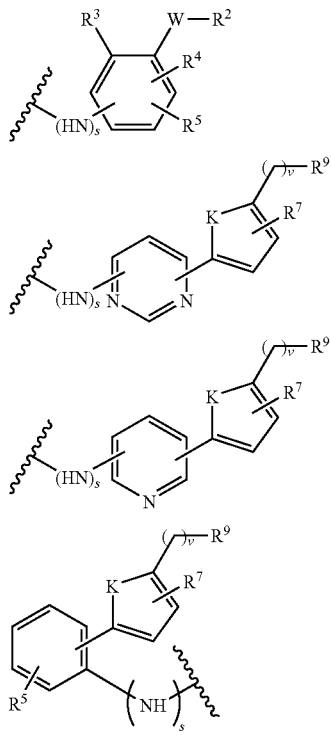

with R⁹ being $CO_2H$, $CO_2$alkyl, $CO_2$aryl, $CO_2NH_2$, $CO_2$aralkyl, $CH_2SO_3H$, $CH_2SO_2NH_2$, $CH_2PO(OH)_2$, 1-H-tetrazolyl, CHO, $COCH_3$, $CH_2OH$, $CH_2NH_2$, $CH_2$NHalkyl, $CH_2$N(alkyl)alkyl', $CH_2OCH_3$, $CH_2SH$, Also preferred are pharmaceutical compositions, wherein the compounds are defined by the formulas (D2) or (D3) or (D5) or (D6).

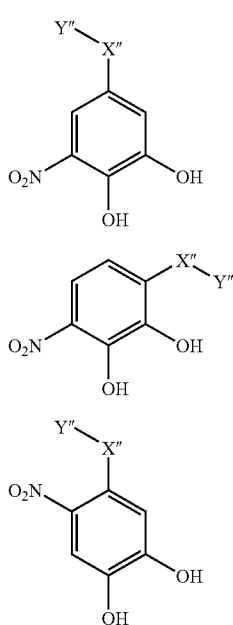

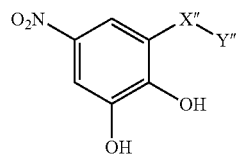

wherein —X"— is as defined above and —Y" is

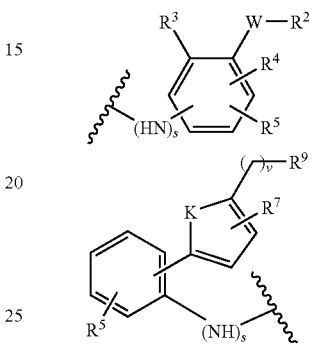

with R⁹ being $CO_2H$, $CO_2$alkyl, $CO_2$aryl, $CO_2NH_2$, $CO_2$aralkyl, $CH_2SO_3H$, $CH_2SO_2NH_2$, $CH_2PO(OH)_2$, 1-H-tetrazolyl, CHO, $COCH_3$, $CH_2OH$, $CH_2NH_2$, $CH_2$NHalkyl, $CH_2$N(alkyl)alkyl', $CH_2OCH_3$, $CH_2SH$, wherein all indices, symbols and substituents are as defined above.

These chemical compounds (C1), (C2), (C3), (C4), (C5), (C6), (D1), (D2), (D3), (D4), (D5), and (D6) are also new compounds for themselves. Chemical compounds having the general structure of formula (C2) or (C3) or (C5) or (C6) or (D2) or (D3) or (D5) or (D6) are preferred.

All compounds as described before present the ability of modulating cell adhesion and modulate selectin—as well as PSGL-1-like mediated binding. The compounds have the ability to modulate the interaction of selectins with sLe$^x$/sLe$^a$ and also the interaction between selectins and tyrosinesulfate residues. As compared to bimosiamose, the leading pan-selectin antagonist, the compounds described here show increased biological activity. Therefore they are useful for the treatment of acute and chronic inflammatory disorders, as well as other medical conditions where selectin mediated processes play a role.

The term "pharmaceutical" includes also diagnostic applications.

The term "pharmaceutical" includes also prophylactic applications in order to prevent medical conditions where selectin mediated processes play a role.

The term "pharmaceutical" includes also applications, where compounds of the present invention may be used as vehicles for drug targeting of diagnostics or therapeutics.

The invention provides pharmaceutical compositions comprising compounds of formulas (Ia) or (Ib) or (Ic) or (Id) or (Ie) or (If) and in a preferred variant of formulas (IIa) or (IIb) or (IIc) or (IId) or (IIe) or (IIf).

In a further preferred variant the invention provides pharmaceutical compositions comprising at least one compound of formula (A1) or (A2) or (A3) or (A4) or (A5) or (A6) or (B1) or (B2) or (B3) or (B4) or (B5) or (B6).

In a particularly preferred variant the invention provides pharmaceutical compositions comprising at least one compound of formula (C1) or (C2) or (C3) or (C4) or (C5) or (C6).

In a very particularly preferred variant the invention provides pharmaceutical compositions comprising at least one compound of formula (D1) or (D2) or (D3) or (D4) or (D5) or (D6).

In a further embodiment of the invention, a compound of formulae (A2), A3, A5, A6, B2, B3, B5, B6, C2, C3, C5, C6, D2, D3, D5 or D6 is used in a composition.

The present invention further provides a method of nodulating the binding of P-selectin, L-selectin or E-selectin to $sLe^x$ or $sLe^a$ and tyrosinesulfate residues comprising the step of administering to a patient an effective amount of at least one compound having the structure of formulas (Ia) or (Ib) or (Ic) or (Id) or (Ie) or (If) to modulate the binding of P-, E- or L-selectin to $sLe^x$ or $sLe^a$ and tyrosinesulfate. It has been found that compounds having the formulas (Ia) or (Ib) or (Ic) or (Id) or (Ie) or (If) shown above act to modulate E-, P- or L-selectin binding.

As used herein the term "alkyl" shall mean a monovalent straight chain or branched chain group of 1 or 2 or 3 or 4 or 5 or 6 or 7 or 8 or 9 or 10 or 11 or 12 carbon atoms including, but not limited to, methyl, ethyl, n-propyl, isopropyl, n-butyl, sec-butyl, tert-butyl and the like. "Alkyl" is independently from each other and can be different or identical.

The term "aryl" shall mean carbocyclic and heterocyclic aromatic groups including, but not limited to, phenyl, 1-naphthyl, 2-naphthyl, fluorenyl, (1,2)-dihydronaphthyl, indenyl, indanyl, thienyl, benzothienyl, thienopyridyl and the like.

The term "aralkyl" (also called arylalkyl) shall mean an aryl group appended to an alkyl group including, but not limited to, benzyl, 1-naphthylmethyl, 2-naphthylmethyl, fluorobenzyl, chlorobenzyl, bromobenzyl, iodobenzyl, alkoxybenzyl (wherein "alkoxy" means methoxy, ethoxy, isopropoxy, n-butoxy, sec-butoxy, tert-butoxy an the like), hydroxybenzyl, aminobenzyl, nitrobenzyl, guanidinobenzyl, fluorenylmethyl, phenylmethyl(benzyl), 1-phenylethyl, 2-phenylethyl, 1-naphthylethyl and the like.

The term "acyl" shall mean —(CHO) or —(C=O)-alkyl or —(C=O)-aryl or —(C=O)-aralkyl including, but not limited to, formyl, acetyl, n-propionyl, isopropionyl, n-butyryl, isobutyryl, pivaloyl, benzoyl, 4-nitrobenzoyl and the like.

The term "pharmaceutically acceptable salts, esters, amides and prodrugs" as used herein refers to those carboxylate salts, amino acid addition salts, esters, amides and prodrugs of the compounds of the present invention which are, within the scope of sound medical judgement, suitable for use in contact with tissues of patients without undue toxicity, irritation, allergic response and the like, commensurate with a reasonable benefit/risk ratio, and effective for their intended use, as well as the zwitterionic forms, where possible, of the compounds of the present invention. The term "salts" refers to the relatively non-toxic, inorganic and organic acid addition salts of the compounds of the present invention. These salts can be prepared in situ during the final isolation and purification of the compounds or by separately reacting the purified compounds in its free form with a suitable inorganic or organic acid or base and isolating the salt thus formed. Representative salts of the compounds of the present invention include the hydrobromide, hydrochloride, sulfate, bisulfate, nitrate, acetate, oxalate, valerate, palmitate, stearate, laurate, borate, benzoate, lactate, phosphate, tosylate, citrate, maleate, fumarate, succinate, tartrate, naphthylate, mesylate, glucoheptonate, lactiobionate, laurylsulphonate salts and the like. These may include cations based on the alkali and alkaline earth metals, such as sodium, lithium, potassium, calcium, magnesium and the like, as well as non-toxic ammonium, quaternary ammonium and amine cations including, but not limited to, ammonium, tetramethylammonium, tetraethylammonium, methylamine, dimethylamine, trimethylamine, triethylamine, ethylamine, and the like.

Examples of the pharmaceutically acceptable, non-toxic esters of the compounds of this invention include $C_1$, $C_2$, $C_3$, $C_4$, $C_5$ and $C_6$ alkyl esters wherein the alkyl group is a straight or branched chain. Acceptable esters also include $C_5$, $C_6$ and $C_7$ cycloalkyl esters as well arylalkyl esters such as, but not limited to benzyl. $C_1$, $C_2$, $C_3$, $C_4$, $C_5$ and $C_6$ alkyl ester are preferred. Esters of the compounds of the present invention may be prepared according to conventional methods.

Examples of pharmaceutically acceptable, non-toxic amides of compounds of this invention include amides derived from ammonia, primary $C_1$, $C_2$, $C_3$, $C_4$, $C_5$ and $C_6$ alkyl amines and secondary $C_1$, $C_2$, $C_3$, $C_4$, $C_5$ and $C_6$ dialkyl amines wherein the alkyl groups are straight or branched chains. In the case of secondary amines the amine may also be in the form of a 5 or 6 membered heterocycle containing one nitrogen atom. Amides derived from ammonia, $C_1$, $C_2$ and $C_3$ alkyl primary amides and $C_1$ to $C_2$ dialkyl secondary amides are preferred. Amides of the compounds of the present invention may be prepared according to conventional methods.

The term "prodrug" refers to one or more compounds that are rapidly transformed in vitro and from a non-active to active state in vivo to yield the parent compound of the above formulas (Ia) or (Ib) or (Ic) or (Id) or (Ie) or (If), for example by hydrolysis in blood or in vivo metabolism.

It is also contemplated that pharmaceutically active compositions may contain a compound of the present invention or other compounds that modulate or compete with E-selectin or P-selectin or L-selectin binding.

Pharmaceutically active compositions of the present invention comprise a pharmaceutically acceptable carrier and a compound of formulas (Ia) or (Ib) or (Ic) or (Id) or (Ie) or (If), whereby a pharmaceutically acceptable carrier can also be a medically appropriate nano-particle, dendrimer, liposome, microbubble or polyethylene glycol (PEG). The pharmaceutical compositions of the present invention may include one or more of the compounds having the above structure (Ia) or (Ib) or (Ic) or (Id) or (Ie) or (If) formulated together with one or more, physiologically acceptable carriers, adjuvants or vehicles, which are collectively referred to herein as carriers, for parenteral injection, for oral administration in solid or liquid form, for rectal or topical administration and the like.

The compositions can be administered to humans and animals either orally, rectally, parenterally (intravenously, intramuscularly, intradermally or subcutaneously), intracisternally, intravaginally, interperitoneally, locally (powders, ointments or drops), or as a buccal or by inhalation (nebulized, or as nasal sprays).

Compositions suitable for parenteral injection may comprise physiologically acceptable sterile aqueous or nonaqueous solutions, stabilizers, antioxidants, preservatives (e.g. ascorbic acid, sodium sulfite, sodium hydrogene sulfite, benzyl alcohol, EDTA), dispersions, suspensions or emulsions and sterile powders for reconstitution into sterile injectable solution or dispersion. Examples of suitable aqueous and nonaqueous carriers, diluents, solvents or vehicles include water, ethanol, polyol, (propylene glycol, polyethylene glycol, glycerol and the like), suitable mixtures thereof, vegetable oils (such as olive or canola oil) and injectable organic esters such as ethyl oleate. Proper fluidity can be maintained, for examples, by the use of a coating such as lecithin, by the maintenance of the required particle size in the case of dispersions and by the use of surfactants.

These compositions may also contain adjuvants such as preserving, wetting, emulsifying, and dispersing agents. Prevention of the actions of microorganisms can be ensured by various antibacterial and antifungal agents, for examples, parabens, chlorobutanol, phenol, sorbic acid, and the like. It may also be desirable to include isotonic agents, for examples sugars, sodium chloride and the like. Prolonged absorption of the injectable pharmaceutical form can be brought about by the use of agents delaying absorption, for examples aluminium monostearate and gelatin.

If desired, and for more effective distribution, the compounds can be incorporated into slow or timed release or targeted delivery systems such as polymer matrices, liposomes, and microspheres. They may be sterilized, for example, by filtration through a bacteria-retaining filter, or by incorporating sterilizing agents in the form of sterile water, or some other sterile injectable medium immediately before use.

Solid dosage forms for oral administration include capsules, tablets, pills, powders and granules. In such solid dosage forms, the active compound or a prodrug is admixed with at least one inert customary excipient (or carrier) such as sodium citrate or dicalcium phosphate or (i) fillers or extenders, as for example, starches, lactose, sucrose, glucose, mannitol and silicic acid, (ii) binders, as for example, carboxymethylcellulose, alginates, gelatine, polyvinylpyrrolidone, sucrose and acacia, (iii) humectants, as for example, glycerol, (div disintegrating agents, as for example, agar-agar, calcium carbonate, potato or tapioca starch, aliginic acid, certain complex silicates and sodium carbonate, (v) solution retarders, as for examples, paraffin, (vi) absorption accelerators, as for example, quaternary ammonium compounds, (vii) wetting agents, as for examples, cetyl alcohol and glycerol monostearate, (viii) adsorbents, as for example, kaolin and bentonite, and (ix) lubricants, as for example, talc, calcium stearate, magnesium stearate, solid polyethylene glycols, sodium lauryl sulfate and mixtures thereof. In the case of capsules, tablets, and pills, the dosage forms may also comprise buffering agents.

Solid compositions of a similar type may also be employed as fillers in soft and hard-filled gelatine capsules using excipients as lactose or milk sugars as well as high molecular polyethylene glycols and the like. Solid dosage forms such as tablets, dragées, capsules, pills and granules can be prepared with coatings and shells, such as enteric coatings and others well known in the art. They may contain opacifying agents, and can also be of such compositions that they release the active compound or compounds in a certain part of the intestinal tract in a delayed manner. Examples of embedding compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, cannola oil, caster oil and sesame seed oil, glycerol, tetrahydrofurfuryl alcohol, polyethylene glycols and fatty acid esters of sorbitan or mixtures of these substances, and the like. Besides such inert diluents, the compositions can also include adjuvants, such as wetting agents, emulsifying and suspending agents, sweeting, flavouring and perfuming agents.

Suspensions, in addition to the active compounds, may contain suspending agents, for example, ethoxylated isostearyl alcohols, polyoxyethylene sorbitol and sorbitan esters, microcrystalline cellulose, aluminium metahydroxide, bentonite, agar-agar, tragacanth or mixtures of these substances and the like.

Compositions for rectal administrations are preferably suppositories, which can be prepared by mixing the compounds of the present invention with suitable nonirritating excipients or carriers such as cacao butter, polyethylene glycol or a suppository wax, which are solid at ordinary temperatures but liquid at body temperature and therefore melt in the rectal or vaginal cavity and release the active component. Dosage forms for topical administration of a compound of this invention include ointments, powder, sprays and inhalants.

The active component is admixed under sterile conditions with a physiologically acceptable carrier and any needed preservatives, buffers or propellants as may be required. Ophthalmic formulations, eye ointments, suspensions, powder and solutions are also contemplated as being within the scope of this invention.

The compounds of the present invention can also be incorporated into or connected to liposomes or administrated in the form of liposomes. As is known in the art, liposomes are generally derived from phospholipids or other lipid substances. Liposomes are formed by mono or multilamellar hydrated liquid crystals that are dispersed in an aqueous medium. Any non-toxic, physiologically acceptable metabolized lipid capable of forming liposomes can be used. The present compositions in liposome form can contain, in addition to the selectin binding antagonists of the present invention, stabilizers, preservatives, excipients and the like. The preferred lipids are the phospholipids and the phosphatidyl cholines (lecithins), both natural and synthetic. Methods to form liposomes are well known in the art.

Non-parenteral dosage forms may also contain a bioavailability enhancing agent (e.g. enzyme modulators, antioxidants) appropriate for the protection of the compounds against degradation. Actual dosage levels of active ingredient in the composition of the present invention may be varied so as to obtain an amount of active ingredient that is effective to obtain the desired therapeutic response for a particular composition and method of administration. The selected dosage level, therefore, depends on the desired therapeutic effect, on the route of administration, on the desired duration of treatment and other factors. The total daily dosage of the compounds on this invention administered to a host in single or divided doses may be in the range up to 50 mg per kilogram of body weight. Dosage unit compositions may contain such submultiples thereof as may be used to make up the daily dosage. It will be understood, however, that the specific dose level for any particular patient, whether human or other animal, will depend upon a variety of factors including the body weight, general health, sex diet, time and route of administration, rates of absorption and excretion, combination with other drugs and the severity of the particular disease being treated.

In particular, the compounds of the present invention may be used to treat a variety of diseases relating to inflammation and cell-cell recognition and adhesion. For example, the compounds of the present invention may be administrated to a patient to treat Chronic Obstructive Pulmonary Disease (COPD), acute lung injury (ALI), cardiopulmonary bypass, acute respiratory distress syndrome (ARDS), Crohn's disease, septic shock, sepsis, chronic inflammatory diseases such as psoriasis, atopic dermatitis, and rheumatoid arthritis, and reperfusion injury that occurs following heart attacks, strokes, atherosclerosis, and organ transplants, traumatic shock, multi-organ failure, autoimmune diseases like multiple sclerosis, percutaneous transluminal angioplasty, asthma and inflammatory bowel disease. In each case, an effective amount of the compounds of the present invention is administered either alone or as part of a pharmaceutically active composition to a patient in need of such treatment. It is also recognized that a combination of the compounds may be administered to a patient in need of such administration. The compounds of the present invention may also be administered to treat other diseases that are associated with cell-cell adhesion. As the present compounds modulate the binding of E-selectin or P-selectin or L-selectin, any disease that is related to this interaction may potentially be treated by the modulation of this binding interaction.

In addition to being found on some white blood cells, $sLe^a$ is found on various cancer cells, including lung and colon cancer cells. It has been suggested that cell adhesion involving $sLe^a$ may be involved in the metastasis of certain cancers and antagonists of $sLe^a$ binding might be useful in treatment of some forms of cancer.

The use of the active ingredients according to the invention or of cosmetic or topical dermatological compositions with an effective content of active ingredient according to the invention surprisingly enables effective treatment, but also prophylaxis of skin ageing caused by extrinsic and intrinsic factors.

The invention particularly relates to the use of a compound of formula (Ia) to (If), particularly (Ib), (Ic), (Ie) or (If) or a stereoisomeric form thereof for the preparation of a cosmetic or dermatological composition.

The amount used of the active compound or a stereoisomeric form thereof corresponds to the amount required to obtain the desired result using the cosmetic or dermatological compositions. One skilled in this art is capable of evaluating this effective amount, which depends on the derivative used, the individual on whom it is applied, and the time of this application. To provide an order of magnitude, in the cosmetic or dermatological compositions according to the invention, the compound of formula (Ib), (Ic), (Ie) or (If) or a stereoisomeric form thereof may be administered in an amount representing from 0.001% to 40% by weight, preferentially 0.005% to 30% by weight and more preferentially from 0.01% to 20% by weight.

A further aspect covers cosmetic compositions comprising a compound of formula (Ib), (Ic), (Ie) or (If) or a stereoisomeric form thereof and at least one cosmetically tolerable component, e.g. a cosmetically tolerable component for skin applications.

The amounts of the various components of the physiological medium of the cosmetic composition according to the invention are those generally included in the fields under consideration. When the cosmetic composition is an emulsion, the proportion of the fatty phase may range from 2% to 80% by weight and preferably from 5% to 50% by weight relative to the total weight of the cosmetic composition.

Thus, the cosmetic composition should contain a non-toxic physiologically acceptable medium that can be applied to human skin. For a topical application to the skin, the cosmetic composition may be in the form of a solution, a suspension, an emulsion or a dispersion of more or less fluid consistency and especially liquid or semi-liquid consistency, obtained by dispersing a fatty phase in an aqueous phase (O/W) or, conversely, (W/O), or alternatively a gel. A cosmetic composition in the form of a mousse or in the form of a spray or an aerosol then comprising a pressurized propellant may also be provided. Also the compositions may be in the form of a haircare lotion, a shampoo or hair conditioner, a liquid or solid soap, a treating mask, or a foaming cream or gel for cleansing the hair. They may also be in the form of hair dye or hair mascara.

The cosmetic compositions of the invention may also comprise one or more other ingredients usually employed in the fields under consideration, selected from among formulation additives, for instance aqueous-phase or oily-phase thickeners or gelling agents, dyestuffs that are soluble in the medium of the cosmetic composition, solid particles such as mineral or organic fillers or pigments in the form of microparticles or nanoparticles, preservatives, fragrances, hydrotopes or electrolytes, neutralizers (acidifying or basifying agents), propellants, anionic, cationic or amphoteric surfactants, polymers, in particular water-soluble or water-dispersible anionic, nonionic, cationic or amphoteric film-forming polymers, mineral or organic salts, chelating agents; mixtures thereof.

The cosmetic compositions may be used to inhibit the micro-inflammatory cycle. Thus, the present invention also relates to cosmetic compositions comprising a compound of formula (Ib), (Ic), (Ie) or (If) or a stereoisomeric form thereof that is used for the cosmetic treatment or cosmetic prophylaxis of micro-inflammatory conditions.

Cosmetic compositions comprising a compound of formula (Ib), (Ic), (Ie) or (If) or a stereoisomeric form thereof that is used for the cosmetic treatment or cosmetic prophylaxis of skin ageing caused by intrinsic factors are also subject of the present invention. Intrinsic factors responsible for skin ageing are genetically programmed determinants including age, hormonal status, and psychological factors.

Beside cosmetically inactive ingredients the cosmetic compositions of the present invention may also comprise one or more cosmetically active ingredients with beneficial action on the skin. Thus, the present invention relates to cosmetic compositions comprising a compound of formula (Ib), (Ic), (Ie) or (If) or a stereoisomeric form thereof and at least one further cosmetically active ingredient, e.g. an UV-blocker or proteins.

Dermatological compositions comprising a compound of formula (Ib), (Ic), (Ie) or (If) or a stereoisomeric form thereof and at least one dermatologically tolerable component, e.g. a dermatologically tolerable component for skin applications, are also subject of the invention.

Dermatologically tolerable components that can be used for the dermatological compositions described here are identical to the cosmetically tolerable components as defined in this invention.

A further embodiment of this invention are dermatological compositions comprising a compound of formula (Ib), (Ic), (Ie) or (If) or a stereoisomeric form thereof that is used for the dermatological treatment, dermatological diagnosis or dermatological prophylaxis of micro-inflammatory conditions.

In particular the invention covers dermatological compositions comprising a compound of formula (Ib), (Ic), (Ie) or (If) or a stereoisomeric form thereof that is used for the dermatological treatment, dermatological diagnosis or dermatological prophylaxis of itching and skin ageing caused by extrinsic factors. Extrinsic factors include environmental factors in general; more particularly photo-ageing due to exposure to the sun, to light or to any other radiation, atmospheric pollution, wounds, infections, traumatisms, anoxia, cigarette smoke, hormonal status as response to external factors, neuropeptides, electromagnetic fields, gravity, lifestyle (e.g.

excessive consumption of alcohol), repetitive facial expressions, sleeping positions, and psychological stressors.

In addition to dermatologically inactive ingredients the dermatological compositions may also comprise dermatologically or pharmaceutically active ingredients. Thus, the present invention also relates to dermatological compositions comprising a compound of formula (Ib), (Ic), (Ie) or (If) or a stereoisomeric form thereof and at least one further dermatologically or pharmaceutically active ingredient. The dermatologically or pharmaceutically active ingredients that can be used for the dermatological compositions described herein are defined as the cosmetically active ingredients defined above. Dermatologically or pharmaceutically active ingredients can be identical to the cosmetically active ingredients as defined in this invention.

Another subject of the present invention are dermatological compositions comprising a compound of formula (Ib), (Ic), (Ie) or (If) or a stereoisomeric form thereof and at least one further dermatologically or pharmaceutically active ingredient characterized in that it is used for the dermatological treatment, dermatological diagnosis or dermatological prophylaxis of micro-inflammatory conditions.

In particular, the present invention relates to dermatological compositions comprising a compound of formula (Ib), (Ic), (Ie) or (If) or a stereoisomeric form thereof and at least one further dermatologically or pharmaceutically active ingredient characterized in that it is used for the dermatological treatment, dermatological diagnosis or dermatological prophylaxis of itching and skin ageing caused by extrinsic factors.

Ageing of the skin may also be caused by a combination of intrinsic and extrinsic factors. Therefore, the present invention also relates to dermatological compositions comprising a compound of formula (Ib), (Ic), (Ie) or (If) or a stereoisomeric form thereof and at least one further pharmaceutically or cosmetically active ingredient characterized in that it is used for the cosmetic and dermatological treatment and cosmetic and dermatological prophylaxis of skin ageing caused by a combination of intrinsic and extrinsic factors.

Another embodiment of this invention is a process for the preparation of a cosmetic composition by mixing a compound of formula (Ib), (Ic), (Ie) or (If) or a stereoisomeric form thereof, at least one cosmetically tolerable component and eventually further cosmetically active ingredients.

In particular, a process for the preparation of a cosmetic composition by mixing a compound of formula (Ib), (Ic), (Ie) or (If) or a stereoisomeric form thereof, at least one cosmetically tolerable component and eventually further cosmetically active ingredients, wherein the composition includes from 0.01% to 20% by weight of compound of formula (Ib), (Ic), (Ie) or (If) or a stereoisomeric form thereof, based on the total weight of the composition is subject of this invention.

A further aspect deals with a process for the preparation of a dermatological composition by mixing a compound of formula (Ib), (Ic), (Ie) or (If) or a stereoisomeric form thereof, at least one dermatologically tolerable component and eventually further pharmaceutically active ingredients.

Many of the compounds of the present invention may be synthesized according to the following general synthetic schemes.

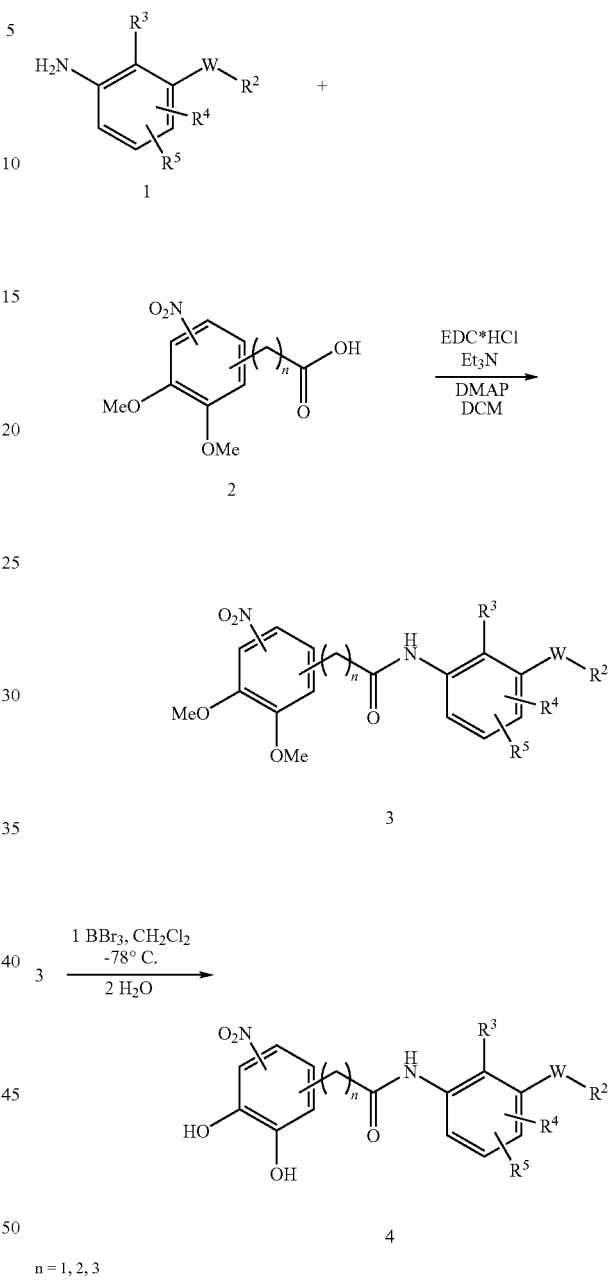

In SCHEME 1 an aniline of type (1) is reacted under inert atmosphere conditions with N'-(3-dimethylaminopropyl)-N-ethyl carbodiimide (EDC), triethylamine, 4-dimethylaminopyridine (DMAP) and a carboxylic acid of type (2) in dichloromethane to give an amide of type (3). Amide of type (3) is further reacted with boron tribromide in dichloromethane at −78° C. to obtain the corresponding 2,4,6-trihydroxyphenyl of type (4). The synthesis sequence shown in SCHEME 1 leading to compounds like (4) is not only reduced to Y—H building blocks like (1) but may be generally applied to all other Y—H type building blocks.

SCHEME 2
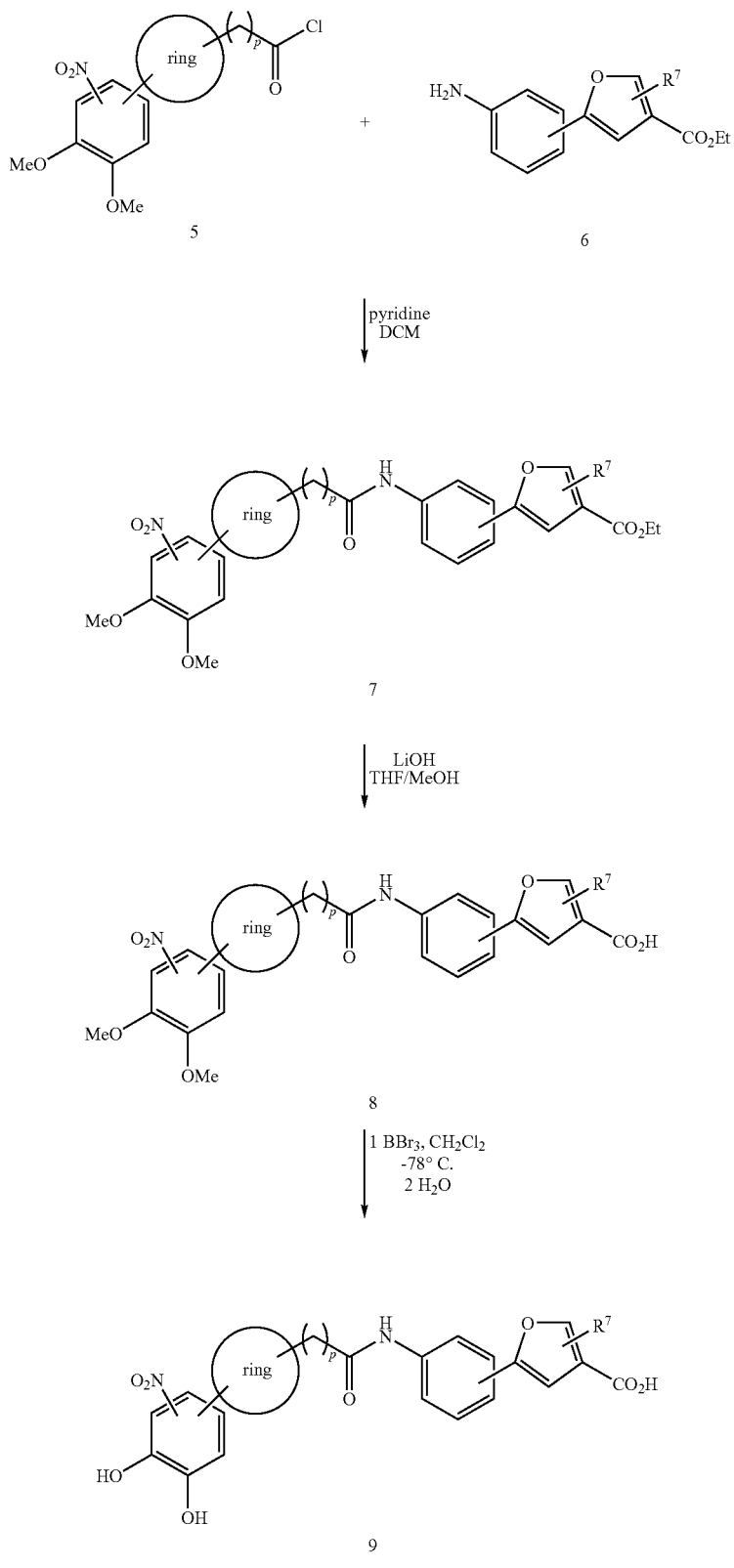
p = 0, 1, 2

In SCHEME 2 an acid chloride like (5) is reacted with an aniline of general type (6) under basic conditions (pyridine in dichloromethane) to form the corresponding anilide (7). Alternatively triethylamine may be used for this reaction step. Ester (7) is hydrolized with LiOH in MeCN or THF/MeOH to obtain a carboxylic acid like (8) which is further reacted with boron tribromide in dichloromethane at −78° C. to obtain after following aqueous workup corresponding demethylated acids of type (9). The synthesis sequence shown in SCHEME 2 leading to compounds like (9) is not only reduced to Y—H building blocks like (6) but may be generally applied to all other Y—H type building blocks.

Building blocks of type (2) or (5) like shown in schemes above may be synthesized like outlined in the following SCHEMES 3 to 9:

corresponding carboxylic acid (17) which is converted to a building block of type (18) by reaction with oxalyl chloride in anhydrous dichloromethane.

SCHEME 4

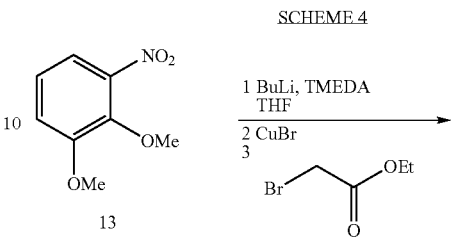

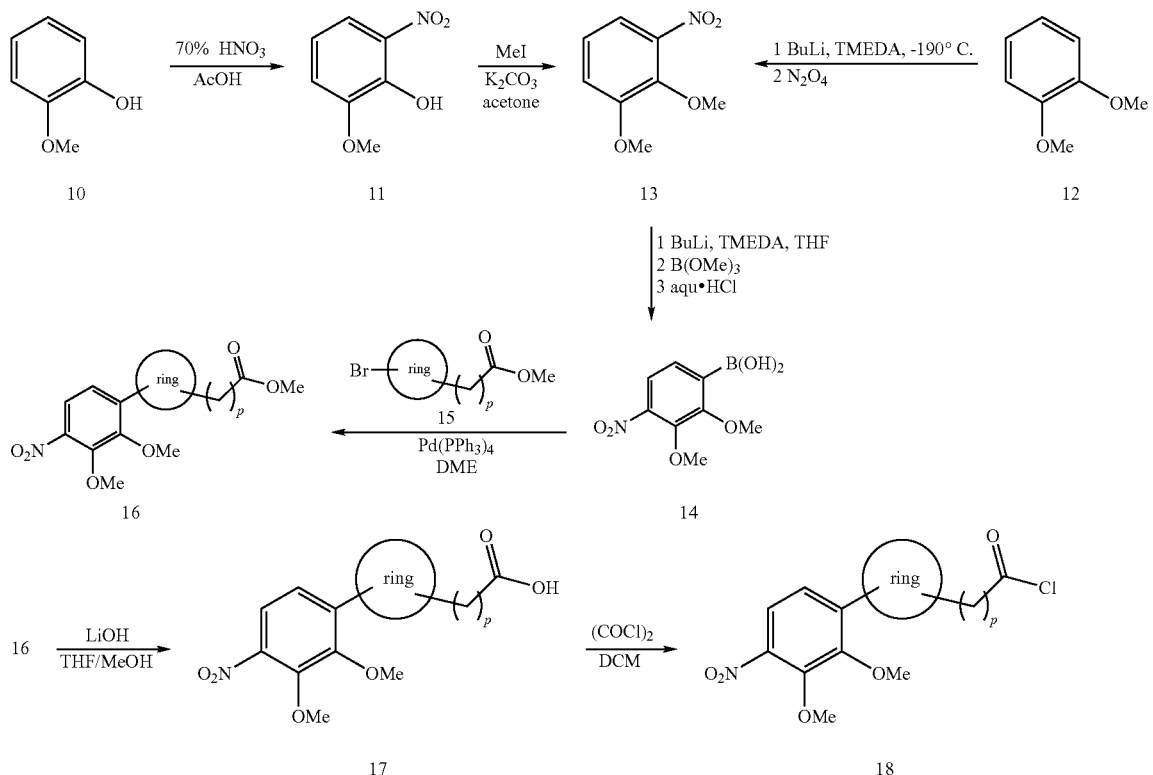

In SCHEME 3 guaiacol (10) is selectively nitrated with 70% HNO₃ in AcOH to give nitroguaiacol (II) which is further methylated with methyl iodide and K₂CO₃ in acetone to give the corresponding veratrol (13). Alternatively (13) is available from veratrol (12) by subsequent reaction with BuLi and N,N,N',N'-tetramethylethylene diamine (TMEDA) at low temperature followed by dinitric tetraoxide. Subsequent reaction of (13) with Buli and TMEDA in THF followed by trimethylborate and hydrochloric acid gives boronic acid (14). Boronic acid (14) is reacted under inert conditions with a brominated aromatic or heteroaromatic ester of generell type (15) under Suzuki-type basic conditions (Pd(PPh₃)₄ and aqueous sodium bicarbonate in dimethoxyethane) to a biaryl of type (16). Biaryl (16) is further hydrolized with aqueous lithium hydroxide in THF and MeOH or MeCN to give the -continued

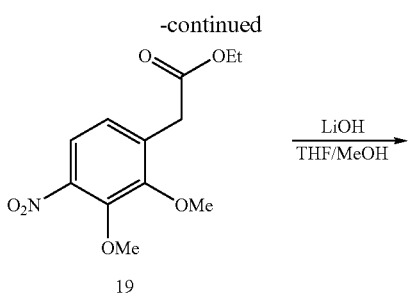

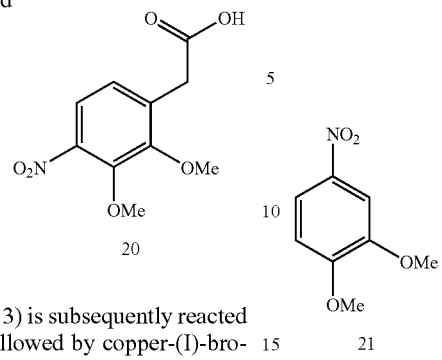

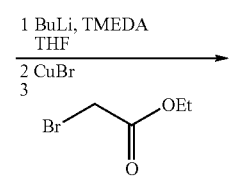

In SCHEME 4 3-nitroveratrol (13) is subsequently reacted with BuLi and TMEDA in THF followed by copper-(I)-bromide and bromoacetic acid ethyl ester to obtain the substituted phenylacetic acid ethyl ester (19) which is further hydrolized with aqueous lithium hydroxide in THF and MeOH or MeCN to give the corresponding carboxylic acid (20).

SCHEME 6

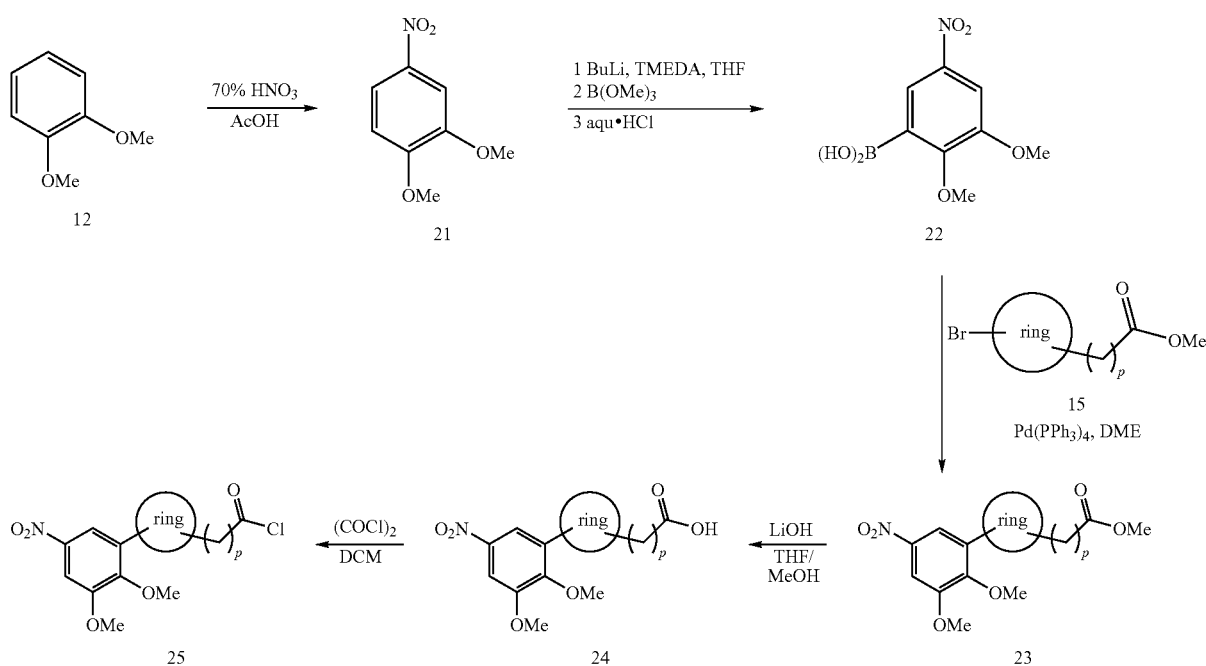

In SCHEME 5 veratrol (12) is selectively nitrated with 70% $HNO_3$ in AcOH to give 4-nitroveratrol (21). Subsequent reaction of (21) with BuLi and TMEDA in THF followed by trimethylborate and hydrochloric acid gives boronic acid (22). Boronic acid (22) is reacted under inert conditions with a brominated aromatic or heteroaromatic ester of generell type (15) under Suzuki-type basic conditions ($Pd(PPh_3)_4$ and aqueous sodium bicarbonate in dimethoxyethane) to a biaryl of type (23). Biaryl (23) is further hydrolized with aqueous lithium hydroxide in THF and MeOH or MeCN to give the corresponding carboxylic acid (24) which is converted to a building block of type (25) by reaction with oxalyl chloride in anhydrous dichloromethane.

-continued

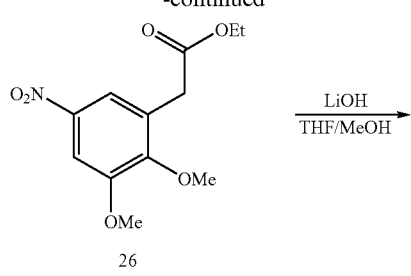

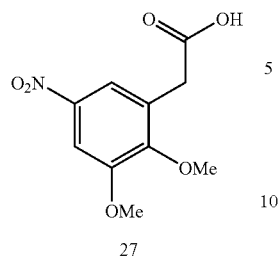

In SCHEME 6 the generation of acid building block (27) is outlined. The synthesis of (27) is analogue to that described in SCHEME 4.

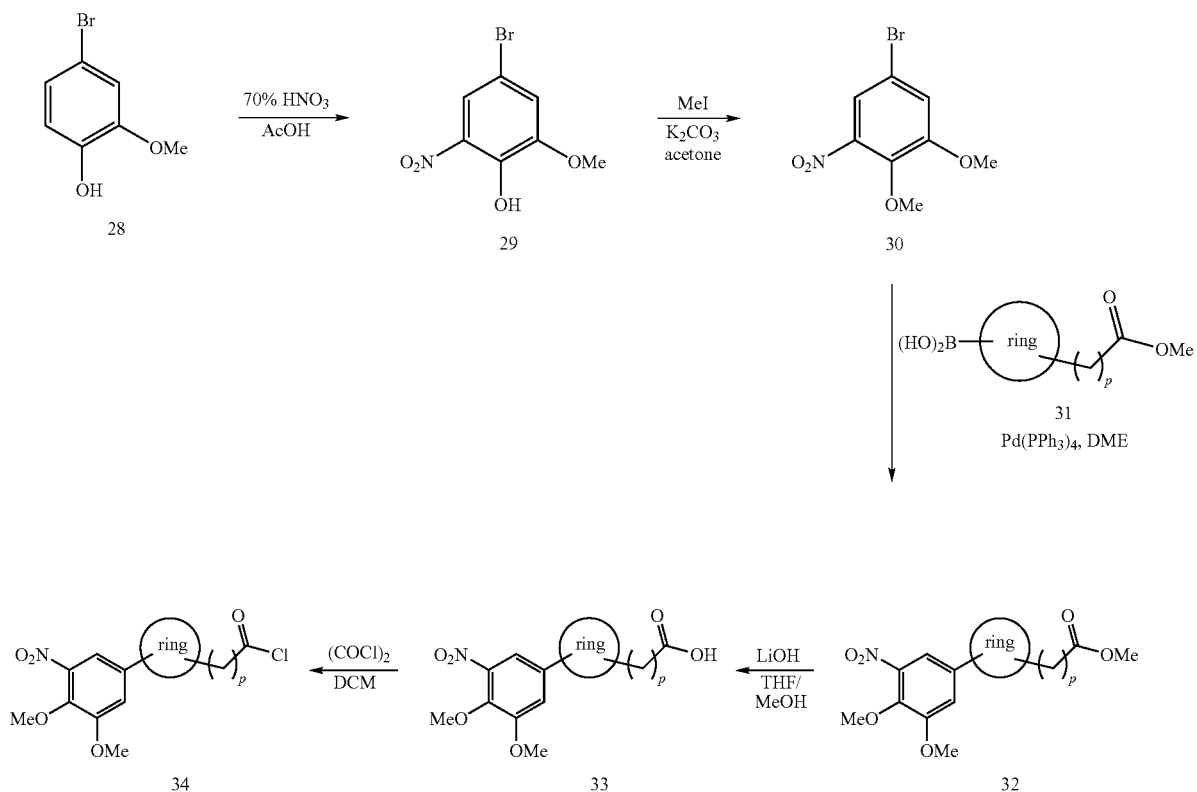

In SCHEME 7 4-bromoguaiacol (28) is selectively nitrated with 70% $HNO_3$ in AcOH to give 4-bromo-6-nitroguaiacol (29) which is further methylated with methyl iodide and $K_2CO_3$ in acetone to give the corresponding 5-bromo-3-nitroveratrol (30). 5-bromo-3-nitroveratrol (30) is reacted under inert conditions with a boronic acid of generell type (31) under Suzuki-type basic conditions ($Pd(PPh_3)_4$ and aqueous sodium bicarbonate in dimethoxyethane) to a biaryl of type (32). Biaryl (32) is further hydrolized with aqueous lithium hydroxide in THF and MeOH or MeCN to give the corresponding carboxylic acid (33) which is converted to a building block of type (34) by reaction with oxalyl chloride in anhydrous dichloromethane.

SCHEME 8

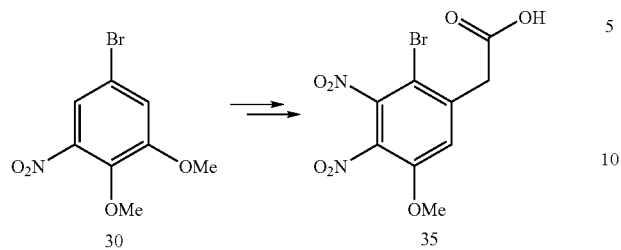

Acid building block (35) outlined in SCHEME 8 is generated from 5-bromo-3-nitroveratrol (30) according to SCHEMES 4 and 6.

SCHEME 9

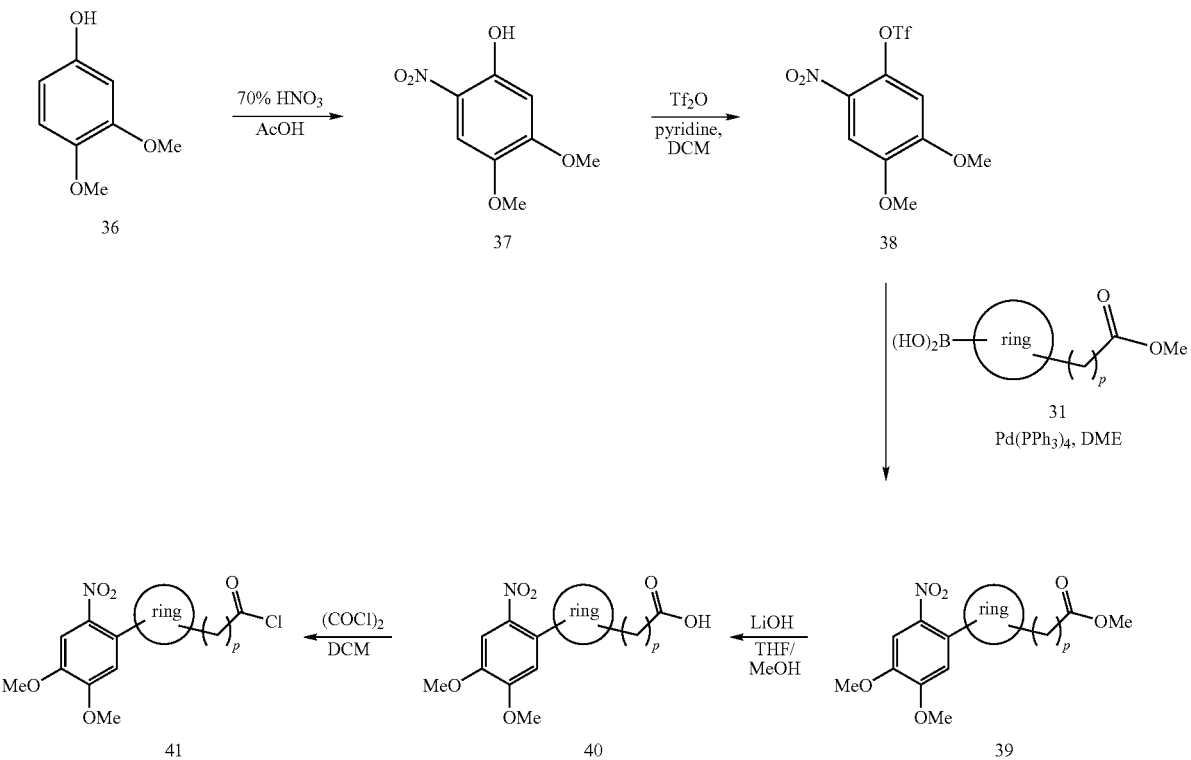

In SCHEME 9 3,4-dimethoxyphenol (36) is selectively nitrated with 70% $HNO_3$ in AcOH to give 4,5-dimethoxy-2-nitrophenol (37) which is further converted to the corresponding triflate (38) with trifluoromethylsulfonic anhydride ($Tf_2O$) and pyridine in dichloromethane. Triflate (38) is reacted under inert conditions with a boronic acid of general type (31) under Suzuki-type basic conditions ($Pd(PPh_3)_4$ and aqueous potassium phosphate in toluene) to a biaryl of type (39). Biaryl (39) is further hydrolized with aqueous lithium hydroxide in THF and MeOH or MeCN to give the corresponding carboxylic acid (40) which is converted to a building block of type (41) by reaction with oxalyl chloride in anhydrous dichloromethane.

EXAMPLE A

Preparation of [5-(2-Amino-phenyl)-thiophen-2-yl]-acetic acid methyl ester (87)

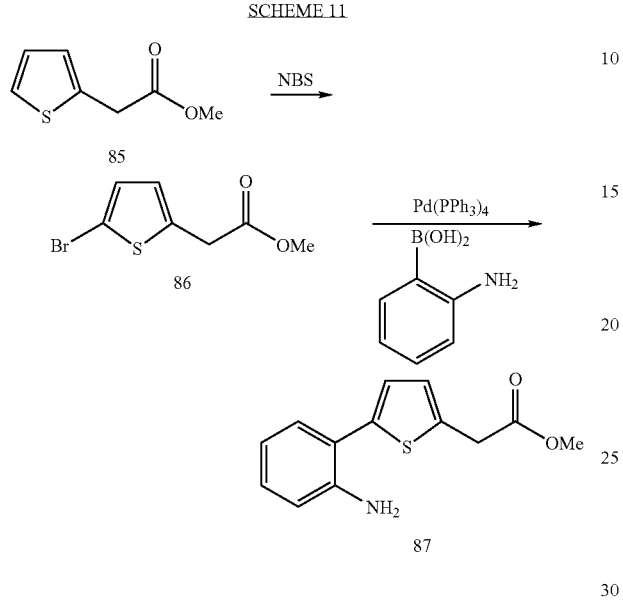

SCHEME 11

Step 1: (The following reaction is carried out in an anhydrous N$_2$ atmosphere.) Dissolve thiophene-2-yl-acetic acid methyl ester (85) (2.0 g, 12.8 mmol) in anhydrous chloroform (9.0 mL) and glacial acetic acid (9.0 mL), add N-bromosuccinimide (2.3 g, 13.0 mmol) in portions and stir the mixture for 3 d at rt. Add water to the reaction mixture, separate layers and extract the aqu. layer with dichloromethane. Wash combined organic layer several times with a 1 M aqu. NaOH and water and once with brine and dry it with Na$_2$SO$_4$. Purify the crude product by preparative radial chromatography (CyH/EtOAc 5+1] to obtain (5-bromo-thiophen-2-yl)-acetic acid methyl ester (86) as a yellow oil (2.46 g, 81%) which is used without any further purification. $^1$H NMR (400 MHz, CDCl$_3$): 3.71 (s, 3H); 3.75 (s, 2H); 6.67 (d, 1H, J=3.8 Hz); 6.88 (d, 1H, J=3.8 Hz).

Step 2: (The following reaction is carried out in an N$_2$ atmosphere.) Ethanol (3.7 mL), tetrakis-(triphenylphosphine)-palladium(0) (289 mg, 0.25 mmol) and Na$_2$CO$_3$ decahydrate (4.0 g, 14.0 mmol) dissolved in water (5.2 mL) are subsequently added to a solution of 2-amino-benzeneboronic acid hydrochloride (910 mg, 5.25 mmol) in toluene (52 mL). Degas the reaction mixture carefully (5 times) and flush with N$_2$ again. A solution of (5-bromo-thiophen-2-yl)-acetic acid methyl ester (1.17 g, 5.0 mmol) in toluene (4.5 mL) is added. Degas the mixture again (5 times) and stir for 22 h at 100° C. Partition the reaction solution between EtOAc and brine and extract the separated aqueous layer with EtOAc (3 times). Wash combined organic layer with water and brine and dry it with Na$_2$SO$_4$. Purify the crude product by preparative radial chromatography (CyH/EtOAc 5+1] to obtain [5-(2-amino-phenyl)-thiophen-2-yl]-acetic acid methyl ester (87) as a brown oil (634 mg, 51%). $^1$H NMR (400 MHz, CDCl$_3$): 3.73 (s, 3H); 3.83 (s, 2H); 3.92-4.07 (br.s, 2H); 6.74 (d, 1H); 6.76 (td, 1H, J$_1$=7.6 Hz, J$_2$=1.3 Hz); 6.92 (d, 1H, J=3.5 Hz); 7.02 (d, 1H, J=3.5 Hz); 7.11 (td, 1H, J$_1$=7.6 Hz, J$_2$=1.5 Hz); 7.23 (dd, 14H, J$_1$=7.6 Hz, J$_2$=1.5 Hz).

EXAMPLE B

Preparation of 5-(2-Amino-phenyl)-thiophene-2-carboxylic acid methyl ester (90)

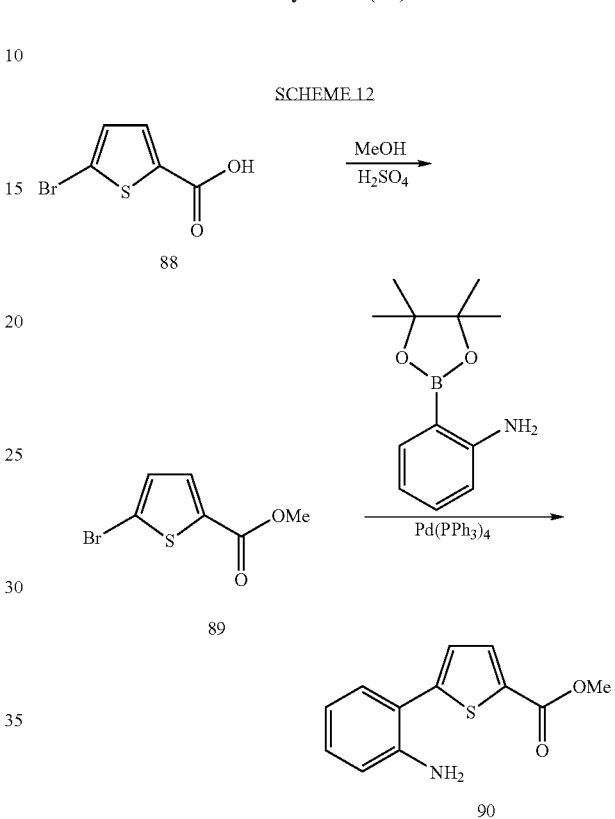

SCHEME 12

Step 1: LE23 Dissolve 5-Bromo-thiophene-2-carboxylic acid (88) (1.50 g, 7.24 mmol) in methanol (10 mL) and add conc. sulfuric acid (0.39 mL, 7.24 mmol). Stir the reaction mixture for 20 h at 75° C. Cool mixture to rt, remove solvent under reduced pressure and resolve the residue in EtOAc. Wash this organic layer 3 times with 5% aqu. Na$_2$CO$_3$ and extract the combined aqueous layer with EtOAc. Wash the combined organic layers with brine and dry with Na$_2$SO$_4$. Remove solvent under reduced pressure and dry the residue without further purification in oil pump vacuum to obtain ester (89) as a white solid (1.48 g, 92%). $^1$H NMR (400 MHz, CDCl$_3$): 3.88 (s, 3H); 4.00 (br.s, 2H); 6.73-6.82 (m, 2H); 7.13-7.21 (m, 2H); 7.26 (dd, 1H, J$_1$=7.6 Hz, J$_2$=1.0 Hz); 7.78 (d, 1H, J=3.8).

Step 2: LE29 (The following reaction is carried out in an N$_2$ atmosphere.) Dissolve Tetrakis-(triphenylphosphine)-palladium(0) (510 mg, 0.45 mmol) and ester (89) (1.97 g, 8.91 mmol) in DME (16 mL), degas the reaction mixture carefully (5 times) and flush with N$_2$. Add 2-(4,4,5,5-Tetramethyl-[1,3,2]dioxaborolan-2-yl)-phenylamine (2.15 g, 9.80 mmol) and a 1 M aqueous NaHCO$_3$ solution (27.0 mL, 27.0 mmol), degas the reaction mixture again carefully (5 times) and flush with N$_2$. Stir the mixture for 18 h at 95° C. Partition the reaction solution between EtOAc and water and extract the separated aqueous layer with EtOAc (3 times). Wash combined organic layer with brine and dry it with Na$_2$SO$_4$. Purify the crude product by flash chromatography (silica gel, CyH/

EtOAc 5+1] to obtain 5-(2-Amino-phenyl)-thiophene-2-carboxylic acid methyl ester (90) as a yellow solid (1.41 g, 67%). $^1$H NMR (400 MHz, CDCl$_3$): 3.88 (s, 3H); 4.00 (br.s, 2H); 6.73-6.82 (m, 2H); 7.13-7.21 (m, 2H); 7.26 (dd, 1H, J$_1$=7.6 Hz, J$_2$=1.0 Hz); 7.78 (d, 1H, J=3.8).

EXAMPLE C

Preparation of 4',5'-Dimethoxy-2'-nitro biphenyl-3-carbonyl chloride (95)

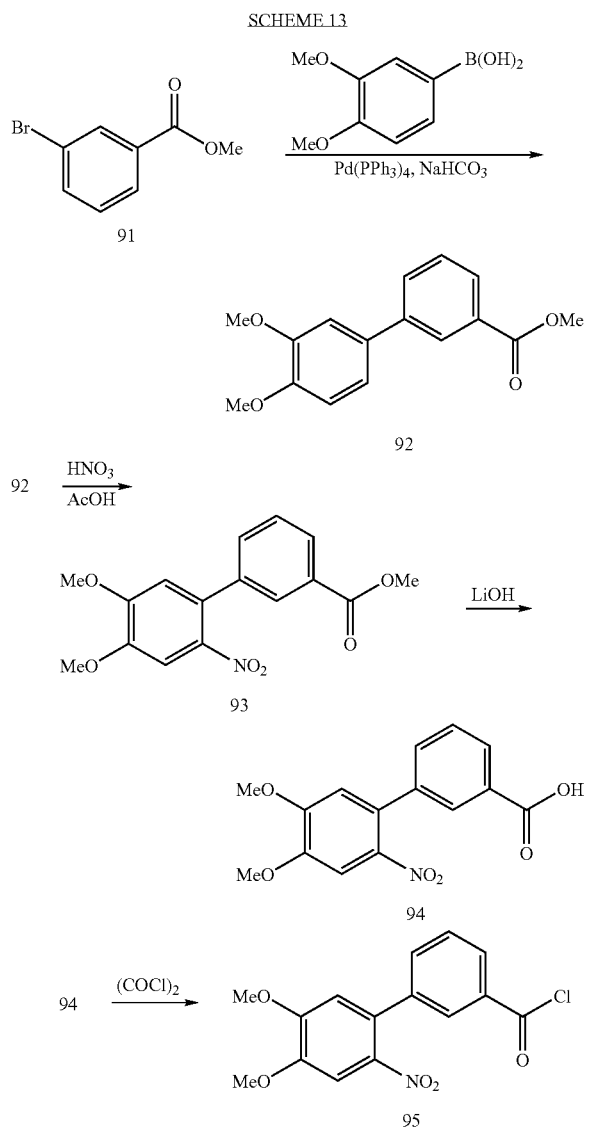

Step 1: DK006 (The following reaction is carried out in an N$_2$ atmosphere.) Dissolve Tetrakis-(triphenylphosphine)-palladium(0) (200 mg, 0.17 mmol) and Methyl 3-bromobenzoate (91) (1.25 mg, 5.81 mmol) in DME (12 mL), degas the reaction mixture carefully (5 times) and flush with N$_2$. Add 3,4-Dimethoxyphenylboronic acid (1.25 g, 6.85 mmol) and a 1 M aqueous NaHCO$_3$ solution (17.7 mL, 17.7 mmol), degas the reaction mixture again carefully (5 times) and flush with N$_2$. Stir the mixture for 2 h at 95° C. Partition the reaction solution between EtOAc and water and extract the separated aqueous layer with EtOAc (4 times). Wash combined organic layer with brine and dry it with Na$_2$SO$_4$. Purify the crude product by flash chromatography (silica gel, CyH/EtOAc 5+1] to obtain the biphenyl (92) as a yellow solid (1.27 g, 80%). $^1$H NMR (400 MHz, CDCl$_3$): 3.92 (s, 3H); 3.93 (s, 3H); 3.95 (s, 3H); 6.94 (d, 1H, J=8.3 Hz); 7.11 (d, 1H, J=1.8 Hz); 7.16 (dd, 1H, J$_1$=8.3 Hz, J$_2$=1.8 Hz); 7.47 (t, 1H, J=7.7 Hz); 7.73 (dt, 1H, J$_1$=7.6 Hz, J$_2$=0.9 Hz); 7.96 (d, 1H, J=7.8 Hz); 8.22 (s, 1H).

Step 2: DK010 Dissolve the biphenyl (92) (653 mg, 2.39 mmol) in glacial acetic acid (32 mL), add 70% nitric acid (1.18 mL, 26.30 mmol) and stir the mixture for 30 min at rt. Add slowly water (12 mL) to the cooled (0° C.) reaction solution, filtrate the precipitate and wash the filter cake carefully with water. Dry the filter cake without further purification in oil pump vacuum followed by desiccator to obtain the nitrated biphenyl (93) as a yellow solid (644 mg, 98%). $^1$H NMR (400 MHz, CDCl$_3$): 3.91 (s, 3H); 3.94 (s, 3H); 3.90 (s, 3H); 6.75 (s, 1H); 7.42-7.51 (m, 2H); 7.60 (s, 1H); 7.97 (t, 1H, J=1.6 Hz); 8.05 (dt, 1H, J$_1$=7.1 Hz, J$_2$=1.6 Hz).

Step 3: DK0011 Dissolve the nitrated biphenyl (93) (1.28 g, 4.70 mmol) in MeCN (46 mL) and add 1M aqu LiOH (23.5 mL, 23.5 mmol). Stir reaction mixture for 20 h at rt. Quench reaction mixture (cooling bath) with 1M aqu. HCl (to get pH ca. 3). Extract the mixture with EtOAc (3×), wash the combined organic layer with brine and dry with Na$_2$SO$_4$. Remove solvent and dry the residue without further purification in oil pump vacuum to obtain carboxylic acid (94) as a yellow solid (1.14 g, 80%). $^1$H NMR (400 MHz, DMSO-d$_6$): 3.89 (s, 3H); 3.90 (s, 3H); 7.01 (s, 1H); 7.53-7.59 (m, 2H); 7.64 (s, 1H); 7.84 (br.s, 1H); 7.93-7.98 (m, 1H).

Step 4: DK012 (The following reaction is carried out in an anhydrous N$_2$ atmosphere.) Dissolve carboxylic acid (94) (550 mg, 1.81 mmol) in anhydrous dichloromethane (13 mL) and add anhydrous DMF (1 mL). Add slowly oxalyl chloride (237 µL, 2.72 mmol) by keeping temperature at ca. 20° C. with a water bath and stir for additional 3 h at rt. Remove solvent and dry the residue in vacuum to obtain crude 4',5'-Dimethoxy-2'-nitro biphenyl-3-carbonyl chloride (95) as a yellow solid. No further purification.

EXAMPLE D

Preparation of 2',3'-Dimethoxy-5'-nitro biphenyl-3-carbonyl chloride (99)

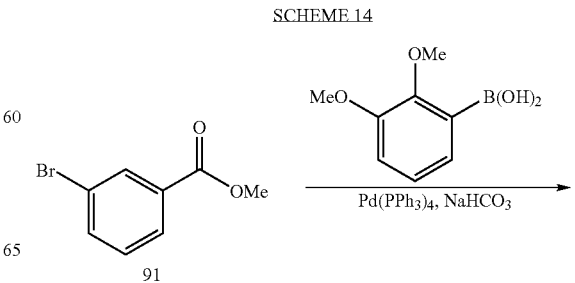

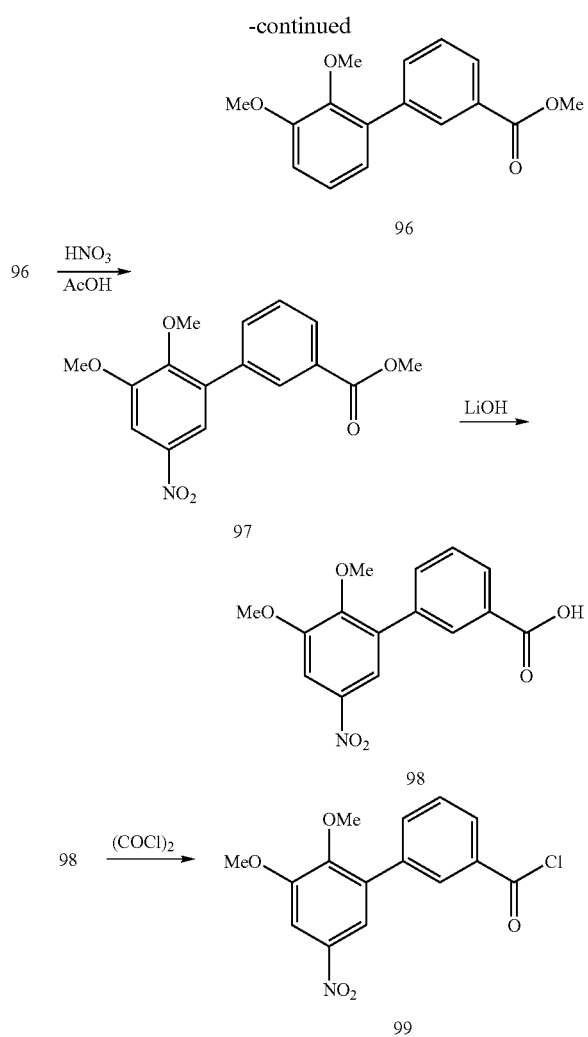

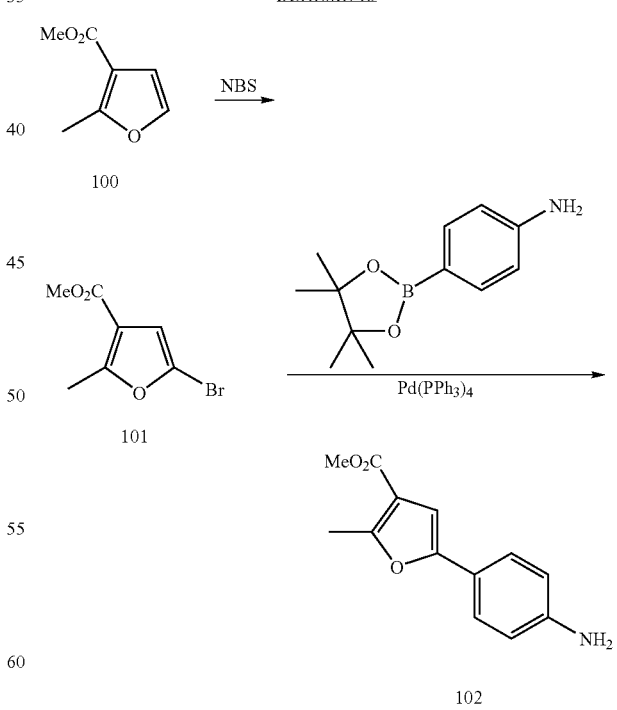

desiccator to obtain the nitrated biphenyl (97) as a yellow solid (1.29 g, 74%). $^1$H NMR (400 MHz, CDCl$_3$): 3.71 (s, 3H); 3.93 (s, 3H); 3.99 (s, 3H); 7.52 (t, 1H, J=7.7 Hz); 7.71 (d, 1H, J=7.8 Hz); 7.80 (d, 1H, J=2.3 Hz); 7.91 (br.d, 1H, J=2.3 Hz); 8.07 (br.d, 1H, J=7.8 Hz); 8.18 (br.s, 1H).

Step 3: FR634 Dissolve the nitrated biphenyl (97) (1.29 g, 4.07 mmol) in MeCN (100 mL) and add 1M aqu LiOH (41 mL, 41 mmol). Stir reaction mixture for 22 h at rt. Quench reaction mixture (cooling bath) with 2M aqu. HCl (to get pH ca. 3). Filtrate the precipitate and wash the filter cake carefully with water and once with EtOAc. Dry the filter cake without further purification in oil pump vacuum followed by desiccator to obtain carboxylic acid (98) as a beige solid (1.06 g, 86%). $^1$H NMR (400 MHz, DMSO-d$_6$): 3.71 (s, 3H); 3.99 (s, 3H); 7.61 (t, 1H, J=7.7 Hz); 7.77 (br.d, 1H, J=7.6 Hz); 7.83 (d, 1H, J=2.8 Hz); 7.89 (d, 1H, J=2.8 Hz); 7.99 (br.d, 1H, J=7.6 Hz); 8.05 (t, 1H, J=1.6 Hz); 13.14 (br.s, 1H).

Step 4: FR637 (The following reaction is carried out in an anhydrous N$_2$ atmosphere.) Dissolve carboxylic acid (98) (500 mg, 1.65 mmol) in anhydrous dichloromethane (11 mL) and add anhydrous DMF (5 mL). Add slowly oxalyl chloride (220 μL, 2.47 mmol) by keeping temperature at ca. 20° C. with a water bath and stir for additional 4 h at rt. Remove solvent and dry the residue in vacuum to obtain crude 2',3'-Dimethoxy-5'-nitro biphenyl-3-carbonyl chloride (99) as a yellow solid. No further purification.

EXAMPLE E 5-(4-Amino-phenyl)-2-methyl-furan-3-carboxylic acid methyl ester (102)

SCHEME 15

Step 1: FR631 (The following reaction is carried out in an N$_2$ atmosphere.) Dissolve Tetrakis-(triphenylphosphine)-palladium(0) (217 mg, 0.19 mmol) and Methyl 3-bromobenzoate (91) (1.35 mg, 6.28 mmol) in DME (13 mL), degas the reaction mixture carefully (5 times) and flush with N$_2$. Add 2,3-Dimethoxyphenylboronic acid (1.33 g, 7.28 mmol) and a 1 M aqueous NaHCO$_3$ solution (19 mL, 19 mmol), degas the reaction mixture again carefully (5 times) and flush with N$_2$. Stir the mixture for 22 h at 100° C. Partition the reaction solution between EtOAc and water and extract the separated aqueous layer with EtOAc (4 times). Wash combined organic layer with brine and dry it with Na$_2$SO$_4$. Purify the crude product by preparative radial chromatography (silica gel, CyH/EtOAc 10+1] to obtain the biphenyl (96) as a white solid (1.50 g, 87%). $^1$H NMR (400 MHz, CDCl$_3$): 3.57 (s, 3H); 3.90 (s, 3H); 3.91 (s, 3H); 6.91-6.96 (m, 2H); 7.11 (t, 1H, J=8.0 Hz); 7.46 (t, 1H, J=7.8 Hz); 7.75 (dt, 1H, J$_1$=7.8 Hz, J$_2$=1.5 Hz); 8.00 (dt, 1H, J$_1$=7.8 Hz, J$_2$=1.4 Hz); 8.19 (t, 1H, J=1.5 Hz).

Step 2: FR632 Dissolve the biphenyl (96) (1.49 g, 5.47 mmol) in glacial acetic acid (30 mL), add 70% nitric acid (0.76 mL, 6.04 mmol) and stir the mixture for 22 h at rt. Pour the reaction solution into ice water, filtrate the precipitate and wash the filter cake carefully with water. Dry the filter cake without further purification in oil pump vacuum followed by Step 1: (The following reaction is carried out under exclusion of light.) Dissolve 2-Methyl-furan-3-carboxylic acid methyl ester (100) (3.60 mL, 28.5 mmol) in chloroform (20 mL) and glacial acetic acid (20 mL) and add NBS (6.90 g, 38.8 mmol) portionwise in between a period of 95 min. Stir the reaction suspension for additional 19 h at rt. Add water to the reaction mixture and extract the aqu. layer with dichloromethane (2 times), wash the combined organic layer with 2M aqu. NaOH, water (3 times) and brine and dry it with $Na_2SO_4$ to obtain 5-Bromo-2-methyl-furan-3-carboxylic acid methyl ester (101) (4.90 g, 78%) as a red brown oil. No further purification. $^1$H NMR (400 MHz, $CDCl_3$): 2.54 (s, 3H); 3.80 (s, 3H); 6.53 (s, 1H).

Step 2: (The following reaction is carried out in a $N_2$ atmosphere.) Dissolve $Pd(PPh_3)_4$ (1.26 g, 1.09 mmol) and 5-Bromo-2-methyl-furan-3-carboxylic acid methyl ester (101) (4.77 g, 21.77 mmol) in DME (116 mL) and stir for 15 min at rt. Add 4-(4,4,5,5-Tetramethyl-[1,3,2]dioxaborolan-2-yl)-phenylamine (5.25 g, 23.96 mmol) followed by an aqu. 1M sodium bicarbonate solution (65.4 mL, 65.3 mmol). Degas the reaction mixture carefully, flush with $N_2$ (5 times) and stir for 4 h at 95° C. (reflux). Cool reaction mixture to rt, remove organic solvent under reduced pressure and partition the residue between water and EtOAc. Extract the aqu. layer with EtOAc (3 times), wash the combined organic layer with water and brine and dry it with $Na_2SO_4$. Purify the obtained crude product by flash chromatography (silica gel, EtOAc/CyH 1+2) to obtain 5-(4-Amino-phenyl)-2-methyl-furan-3-carboxylic acid methyl ester (102) (2.35 g, 46%) as a yellow-brown solid. $^1$H NMR (400 MHz, $CDCl_3$): 2.60 (s, 3H); 3.74 (br.s, 2H); 3.82 (s, 3H); 6.64 (s, 1H); 6.67 (dt, 1H, $J_1$=8.6 Hz, $J_2$=2.3 Hz); 7.42 (dt, 2H, $J_1$=8.8 Hz, $J_2$=2.3 Hz).

EXAMPLE F (3,4-Dimethoxy-5-nitro-phenyl)-acetic acid (107)

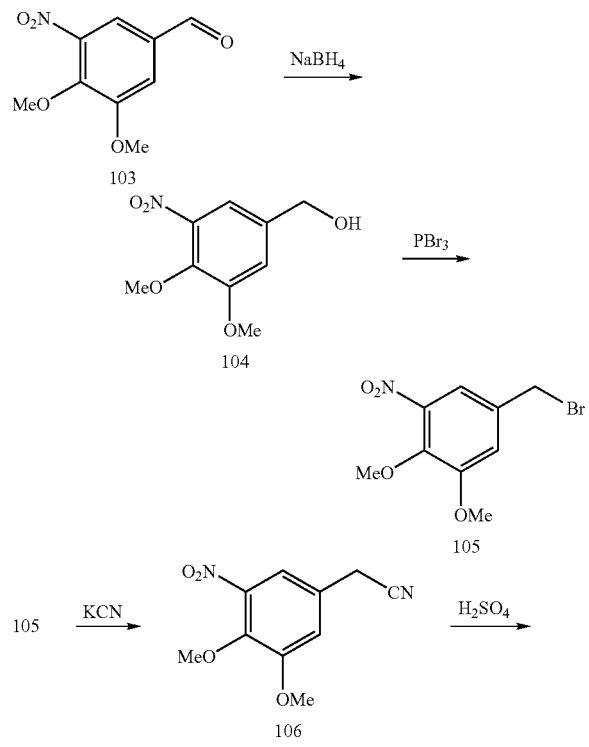

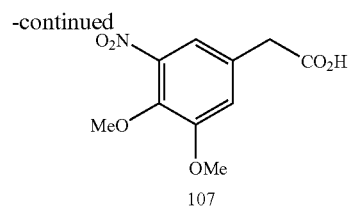

Step 1: (The following reaction is carried out under exclusion of light.) Dissolve the aldehyde (103) (877 mg, 4.15 mmol) in MeOH (30 mL), cool the solution to 0° C. and add portionwise sodium borohydrate (548 mg, 14.49 mmol) in between a period of 40 min. Stir the reaction solution for additional 70 min at rt. Cool the mixture to 0° C., add slowly a 1M HCl (20 mL) and remove solvent. Partition the residue between water and EtOAc. Extract the aqu. layer with EtOAc (3 times), wash the combined organic layer with brine and dry it with $Na_2SO_4$. Remove solvent to obtain the benzylic alcohol (104) (876 mg, 99%) as a brown solid. No further purification. $^1$H NMR (400 MHz, $CDCl_3$): 3.92 (s, 3H); 3.95 (s, 3H); 4.68 (s, 2H); 7.14 (d, 1H, J=1.8 Hz); 7.29 (d, 1H, J=1.8 Hz).

Step 2: (The following reaction is carried out in a 3-necked flask equipped with reflux condenser and dropping funnel under an anhydrous $N_2$ atmosphere.) Dissolve phosphorous tribromide (800 µL, 8.52 mmol) in anhydrous toluene (90 mL) and heat the solution to 80° C. Add slowly a suspension of benzylic alcohol (104) (1.82 g, 8.52 mmol) in anhydrous toluene (80 mL) and stir the reaction mixture for additional 2 h at 80° C. Cool the mixture down with an ice bath and add slowly ice water to the reaction solution. Partition the mixture between water and EtOAc. Extract the aqu. layer with EtOAc (3 times), wash the combined organic layer with water and brine and dry it with $Na_2SO_4$. Remove solvent to obtain the benzyl bromide (105) (2.23 g, 95%) as a brown solid. No further purification. $^1$H NMR (400 MHz, $CDCl_3$): 3.92 (s, 3H); 3.96 (s, 3H); 4.42 (s, 2H); 7.10 (d, 1H, J=2.0 Hz); 7.34 (d, 1H, J=2.0 Hz).

Step 3: Dissolve benzyl bromide (105) (2.22 g, 8.06 mmol) in MeOH (44.0 mL) and water (9.0 mL), add potassium cyanide (787 mg, 12.09 mmol) and stir the reaction mixture for additional 90 min at 75° C. (reflux). Partition the mixture between water and EtOAc. Extract the aqu. layer with EtOAc (3 times), wash the combined organic layer with a saturated sodium bicarbonate solution (3 times) and brine and dry it with $Na_2SO_4$. Purify the crude product by preparative radial chromatography (silica gel, CyH/EtOAc 2+1] to obtain the nitrile (106) as a yellow solid (1.35 g, 75%). $^1$H NMR (400 MHz, $CDCl_3$): 3.74 (s, 2H); 3.94 (s, 3H); 3.96 (s, 3H); 7.06 (d, 1H, J=2.0 Hz); 7.26 (d, 1H, J=2.0 Hz).

Step 4: Suspend nitrile (106) (1.35 g, 6.07 mmol) in glacial acetic acid (53 mL) and water (65 mL), add slowly conc. sulphuric acid (22 mL) and stir the reaction mixture for additional 18 h under reflux. Extract the cooled reaction mixture with EtOAc (5 times), wash the combined organic layer with water (5 times) and brine and dry it with $Na_2SO_4$. Remove solvent to (3,4-Dimethoxy-5-nitro-phenyl)-acetic acid (107) (1.46 g, 99%) as a yellow solid. No further purification. $^1$H NMR (400 MHz, DMSO-$d_6$): 3.64 (s, 2H); 3.83 (s, 3H); 3.87 (s, 3H); 7.30 (s, 2H); 12.45 (br.s, 1H).

EXAMPLE 1

(5-{2-[2-(4,5-Dihydroxy-2-nitro-phenyl)-acetylamino]-phenyl}-thiophen-2-yl)-acetic acid (110)

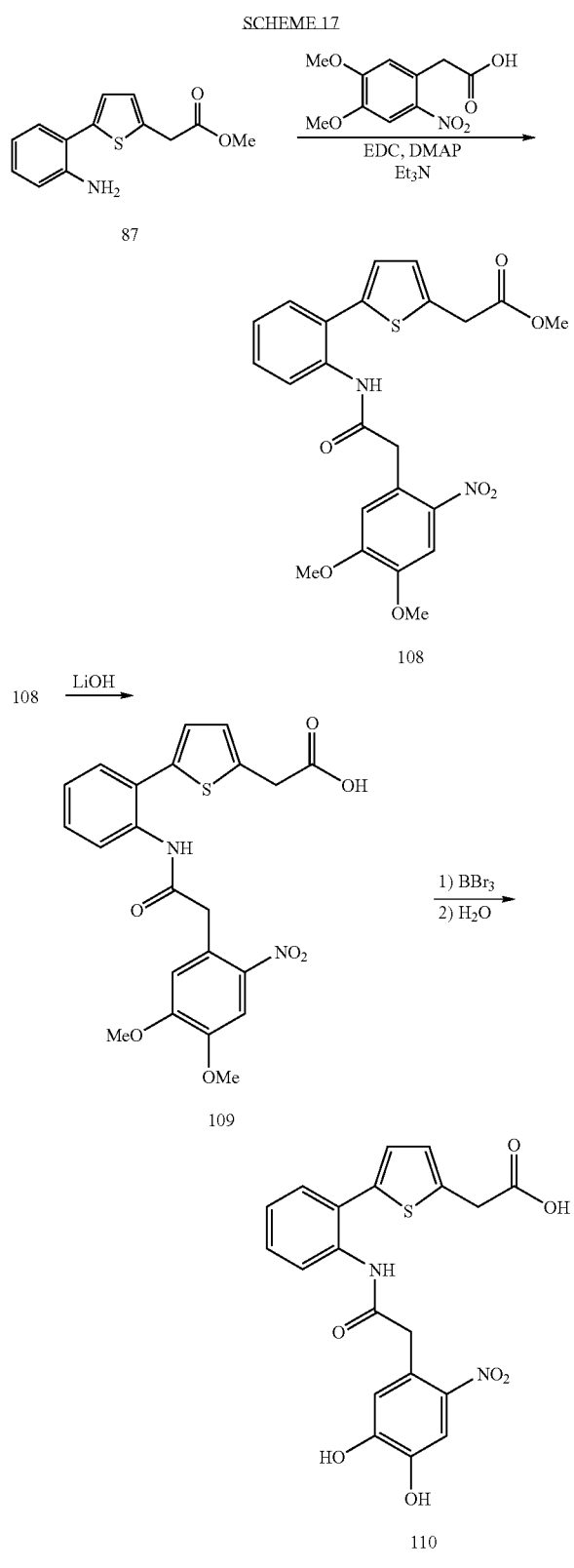

Step 1 (The following reaction is done in an anhydrous N₂ atmosphere.) Suspend EDC hydrochloride (58 mg, 0.30 mmol) in anhydrous dichloromethane (1.0 mL), add triethylamine (0.042 mL, 0.30 mmol) and stir for 10 min at rt. Add (4,5-Dimethoxy-2-nitro-phenyl)-acetic acid (54 mg, 0.22 mmol) and DMAP (8 mg, 0.06 mmol) and stir for 15 min. Add aniline (87) (50 mg, 0.20 mmol) and stir the reaction solution 22 h at 40° C.

Partition the reaction solution between dichloromethane and water (1+1), separate layers and extract aqu. layer with dichloromethane (3 times). Wash the combined organic layer with brine and dry with Na₂SO₄. Purify crude product by preparative radial chromatography (silica gel 60 PF, CyH/EtOAc 3+1) to obtain product (108) as yellow-white solid (28 mg, 30%). ¹H NMR (400 MHz, CDCl₃): 3.75 (s, 3H); 3.82 (s, 2H); 3.92 (s, 2H); 3.94 (s, 3H); 3.96 (s, 3H); 6.75 (d, 1H, J=3.3 Hz); 6.80-6.84 (m, 2H); 7.09 (t, 1H, J=7.5 Hz); 7.27-7.35 (m, 2H); 7.63 (s, 1H); 7.89 (s, 1H); 8.27 (d, 1H, J=7.8 Hz).

Step 2: Dissolve ester (108) (49 mg, 0.10 mmol) in methanol (1.3 mL) and THF (3.8 mL), add a 1M aqu. LiOH solution (0.52 mL, 0.52 mmol) and stir 20 h at 40° C. Remove solvent under reduced pressure und partition residue between EtOAc and 1 M HCl (1+1). Separate the aqueous layer and extract 3 times with EtOAc. Wash the combined organic layer with brine and dry with Na₂SO₄. Remove solvent under reduced pressure and dry the residue without further purification in oil pump vacuum to obtain crude product (109) as light brown solid (48 mg, quant.). ¹H NMR (400 MHz, CDCl₃): 3.87 (s, 2H); 3.92 (s, 2H); 3.94 (s, 3H); 3.96 (s, 3H); 6.76 (d, 1H, J=3.3 Hz); 6.82 (s, 1H); 6.85 (d, 1H, J=3.3 Hz); 7.09 (t, 1H, J=7.7 Hz); 7.26-7.35 (m, 2H); 7.63 (s, 1H); 7.88 (br.s, 1H); 8.28 (d, 1H, J=8.1 Hz).

Step 3: (The following reaction is done in an anhydrous N₂ atmosphere.) Dissolve carboxylic acid (109) (48 mg, 0.10 mmol) in anhydrous dichloromethane (3.0 mL), cool to −78° C. (acetone/dry ice) and add slowly a 1M BBr₃ solution in dichloromethane (0.42 mL, 0.42 mmol). Stir the reaction mixture for additional 30 min at −78° C. Remove cooling bath and stir the reaction mixture for 1.5 h at 0° C. and further 2 h at rt. Cool reaction mixture to 0° C., add slowly water (1.00 mL) under vigorous stirring. Partition the reaction mixture between EtOAc and water (1+1). Extract the separated aqueous layer with EtOAc (2 times) and wash the combined organic layer with brine and dry with Na₂SO₄. Remove solvent under reduced pressure and purify crude product by preparative RP HPLC (gradient, water/CH₃CN 95:5 to 5:95) to obtain (5-{2-[2-(4,5-Dihydroxy-2-nitro-phenyl)-acetylamino]-phenyl}-thiophen-2-yl)-acetic acid (110) as a yellow-brown solid (10 mg, 23%). ¹H NMR (400 MHz, CD₃OD): 3.88 (s, 2H); 3.96 (s, 2H); 6.83 (s, 1H); 6.91 (d, 1H, J=3.3 Hz); 6.93 (d, 1H, J=3.5 Hz); 7.23 (t, 1H, J=7.5 Hz); 7.35 (t, 1H, J=7.8 Hz); 7.45 (d, 1H, J=7.8 Hz); 7.66 (s, 1H); 7.85 (d, 1H, J=8.1 Hz).

EXAMPLE 2

2-Methyl-5-{4-[(2'-nitro-4',5'-dihydroxy-biphenyl-3-carbonyl)-amino]-phenyl}-furan-3-carboxylic acid (113)

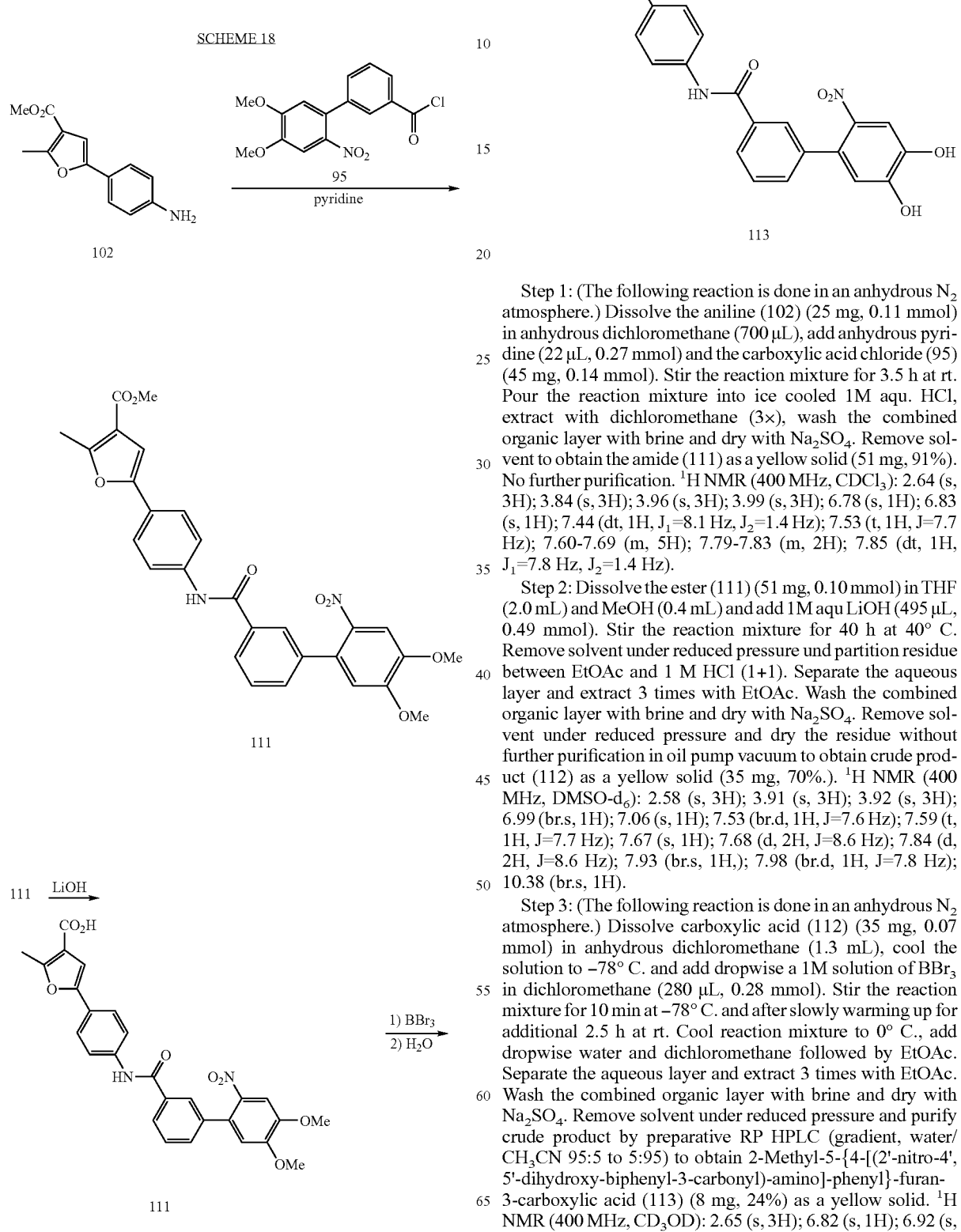

Step 1: (The following reaction is done in an anhydrous N₂ atmosphere.) Dissolve the aniline (102) (25 mg, 0.11 mmol) in anhydrous dichloromethane (700 µL), add anhydrous pyridine (22 µL, 0.27 mmol) and the carboxylic acid chloride (95) (45 mg, 0.14 mmol). Stir the reaction mixture for 3.5 h at rt. Pour the reaction mixture into ice cooled 1M aqu. HCl, extract with dichloromethane (3×), wash the combined organic layer with brine and dry with Na₂SO₄. Remove solvent to obtain the amide (111) as a yellow solid (51 mg, 91%). No further purification. ¹H NMR (400 MHz, CDCl₃): 2.64 (s, 3H); 3.84 (s, 3H); 3.96 (s, 3H); 3.99 (s, 3H); 6.78 (s, 1H); 6.83 (s, 1H); 7.44 (dt, 1H, $J_1$=8.1 Hz, $J_2$=1.4 Hz); 7.53 (t, 1H, J=7.7 Hz); 7.60-7.69 (m, 5H); 7.79-7.83 (m, 2H); 7.85 (dt, 1H, $J_1$=7.8 Hz, $J_2$=1.4 Hz).

Step 2: Dissolve the ester (111) (51 mg, 0.10 mmol) in THF (2.0 mL) and MeOH (0.4 mL) and add 1M aqu LiOH (495 µL, 0.49 mmol). Stir the reaction mixture for 40 h at 40° C. Remove solvent under reduced pressure und partition residue between EtOAc and 1 M HCl (1+1). Separate the aqueous layer and extract 3 times with EtOAc. Wash the combined organic layer with brine and dry with Na₂SO₄. Remove solvent under reduced pressure and dry the residue without further purification in oil pump vacuum to obtain crude product (112) as a yellow solid (35 mg, 70%.). ¹H NMR (400 MHz, DMSO-d₆): 2.58 (s, 3H); 3.91 (s, 3H); 3.92 (s, 3H); 6.99 (br.s, 1H); 7.06 (s, 1H); 7.53 (br.d, 1H, J=7.6 Hz); 7.59 (t, 1H, J=7.7 Hz); 7.67 (s, 1H); 7.68 (d, 2H, J=8.6 Hz); 7.84 (d, 2H, J=8.6 Hz); 7.93 (br.s, 1H,); 7.98 (br.d, 1H, J=7.8 Hz); 10.38 (br.s, 1H).

Step 3: (The following reaction is done in an anhydrous N₂ atmosphere.) Dissolve carboxylic acid (112) (35 mg, 0.07 mmol) in anhydrous dichloromethane (1.3 mL), cool the solution to −78° C. and add dropwise a 1M solution of BBr₃ in dichloromethane (280 µL, 0.28 mmol). Stir the reaction mixture for 10 min at −78° C. and after slowly warming up for additional 2.5 h at rt. Cool reaction mixture to 0° C., add dropwise water and dichloromethane followed by EtOAc. Separate the aqueous layer and extract 3 times with EtOAc. Wash the combined organic layer with brine and dry with Na₂SO₄. Remove solvent under reduced pressure and purify crude product by preparative RP HPLC (gradient, water/CH₃CN 95:5 to 5:95) to obtain 2-Methyl-5-{4-[(2'-nitro-4',5'-dihydroxy-biphenyl-3-carbonyl)-amino]-phenyl}-furan-3-carboxylic acid (113) (8 mg, 24%) as a yellow solid. ¹H NMR (400 MHz, CD₃OD): 2.65 (s, 3H); 6.82 (s, 1H); 6.92 (s, 1H); 7.48 (dt, 1H, $J_1$=7.8 Hz, $J_2$=1.4 Hz); 7.57 (t, 1H, J=7.7

Hz); 7.57 (s, 1H); 7.69 (d, 2H, J=8.8 Hz); 7.78 (d, 2H, J=8.8 Hz); 7.89 (t, 1H, J=1.6 Hz); 7.97 (dt, 1H, J$_1$=8.1 Hz, J$_2$=1.4 Hz).

EXAMPLE 3

(5-{2-[(2',3'-Dihydroxy-5'-nitro-biphenyl-3-carbonyl)-amino]-phenyl}-thiophen-2-yl)-acetic acid (116)

SCHEME 19

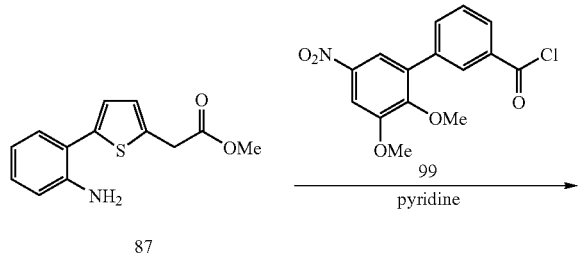

87    99 pyridine

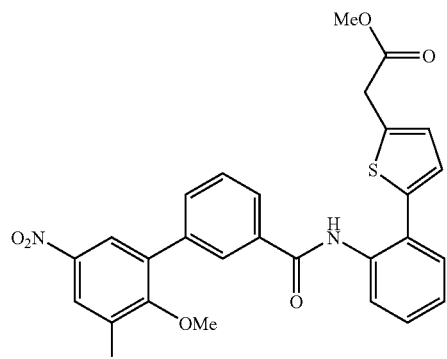

114

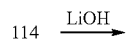 LiOH

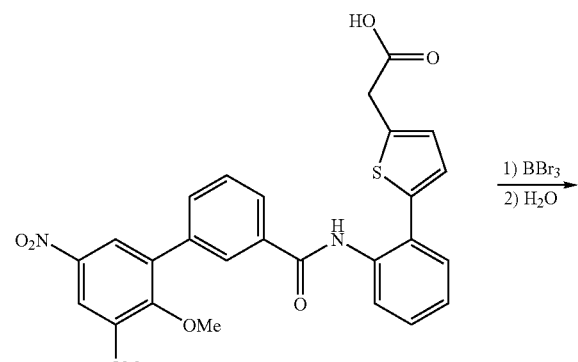

 1) BBr$_3$
2) H$_2$O

115

-continued

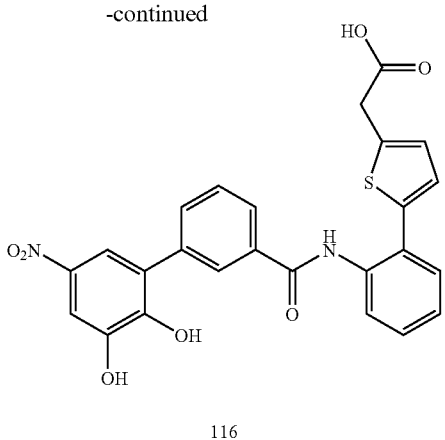

116

Step 1: (The following reaction is done in an anhydrous N$_2$ atmosphere.) Dissolve the aniline (87) (100 mg, 0.40 mmol) in anhydrous dichloromethane (3.0 mL), add anhydrous pyridine (80 µL, 1.01 mmol) and the carboxylic acid chloride (99) (169 mg, 0.53 mmol). Stir the reaction mixture for 20 h at rt. Pour the reaction mixture into ice cooled 1M aqu. HCl, extract with dichloromethane (3×), wash the combined organic layer with brine and dry with Na$_2$SO$_4$. Purify crude product by preparative radial chromatography (silica gel 60PF, CyH/EtOAc 3+1) to obtain the amide (114) as a yellow solid (184 mg, 85%). $^1$H NMR (400 MHz, CDCl$_3$): 3.69 (s, 3H); 3.71 (s, 3H); 3.86 (s, 2H); 4.00 (s, 3H); 6.98 (d, 1H, J=3.3 Hz); 7.03 (d, 1H, J=3.5 Hz); 7.17 (td, 1H, J$_1$=7.6 Hz, J$_2$=1.0 Hz); 7.38-7.44 (m, 2H); 7.53 (t, 1H, J=7.7 Hz); 7.68 (dt, 1H, J$_1$=7.8 Hz, J$_2$=1.3 Hz); 7.78 (dt, 1H, J$_1$=7.8 Hz, J$_2$=1.3 Hz); 7.80 (d, 1H, J=2.5 Hz); 7.88 (d, 1H, J=2.5 Hz); 7.91 (t, 1H, J=3.0 Hz); 8.43 (br.s, 1H); 8.51 (d, 1H, J=8.6 Hz).

Step 2: Dissolve the ester (114) (184 mg, 0.34 mmol) in MeCN (5.0 mL) and MeOH (2.0 mL) and add 1M aqu LiOH (1.7 mL, 1.7 mmol). Stir the reaction mixture for 20 h at rt. Remove solvent under reduced pressure und partition residue between EtOAc and 1 M HCl (1+1). Separate the aqueous layer and extract 3 times with EtOAc. Wash the combined organic layer with brine and dry with Na$_2$SO$_4$. Remove solvent under reduced pressure and dry the residue without further purification in oil pump vacuum to obtain crude product (115) as a light yellow solid (183 mg, quant.). $^1$H NMR (400 MHz, CD$_3$OD): 3.78 (s, 3H); 3.85 (s, 2H); 4.07 (s, 3H); 6.98 (d, 1H, J=3.5 Hz); 7.19 (d, 1H, J=3.5 Hz); 7.38 (td, 1H, J$_1$=7.5 Hz, J$_2$=1.3 Hz); 7.44 (td, 1H, J$_1$=7.7 Hz, J$_2$=1.5 Hz); 7.61-7.68 (m, 2H); 7.73 (d, 1H, J=8.1 Hz); 7.80 (dd, 1H, J$_1$=7.6 Hz, J$_2$=1.3 Hz); 7.94-8.02 (m, 3H); 8.10 (br.s, 1H).

Step 3: (The following reaction is done in an anhydrous N$_2$ atmosphere.) Dissolve carboxylic acid (115) (70 mg, 0.14 mmol) in anhydrous dichloromethane (1.4 mL), cool the solution to −78° C. and add dropwise a 1M solution of BBr$_3$ in dichloromethane (810 µL, 0.81 mmol). Stir the reaction mixture for 10 min at −78° C. and after slowly warming up for additional 2 h at rt. Cool reaction mixture to 0° C., add dropwise water and dichloromethane followed by EtOAc. Separate the aqueous layer and extract 3 times with EtOAc. Wash the combined organic layer with brine and dry with Na$_2$SO$_4$. Remove solvent under reduced pressure and purify crude product by preparative RP HPLC (gradient, water/CH$_3$CN 95:5 to 5:95) to obtain (5-{2-[(2',3'-Dihydroxy-5'-nitro-biphenyl-3-carbonyl)-amino]-phenyl}-thiophen-2-yl)-acetic acid (116) (12 mg, 18%) as a brown solid. $^1$H NMR (400 MHz, CD$_3$OD): 3.84 (s, 2H); 6.99 (d, 1H, J=2.8 Hz); 7.19 (d, 1H, J=3.5 Hz); 7.37 (td, 1H, J$_1$=7.8 Hz, J$_2$=1.5 Hz) 7.44 (td, 1H, J$_1$=7.7 Hz, J$_2$=1.5 Hz); 7.58-7.65 (m, 2H); 7.72-7.76 (m, 2H); 7.86-7.97 (m, 3H); 8.16 (br.s, 1H).

EXAMPLE 4

4',5'-Dihydroxy-2'-nitro-biphenyl-3-carboxylic acid phenylamide (117)

SCHEME 20

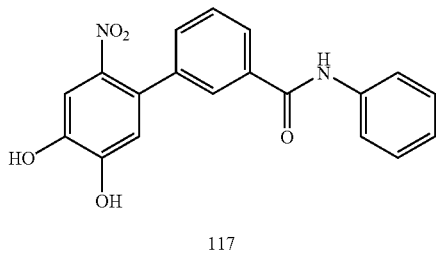

117

4',5'-Dihydroxy-2'-nitro-biphenyl-3-carboxylic acid phenylamide (117) is made starting from aniline and carboxylic acid chloride (95) according to the procedure described above in steps 1 and 3 of EXAMPLE 3 to obtain 4',5'-Dihydroxy-2'-nitro-biphenyl-3-carboxylic acid phenylamide (117) (2.4 mg, 10% over 2 steps) as a brown solid. $^1$H NMR (400 MHz, CD$_3$OD): 6.84 (s, 1H); 7.19 (br.t, 1H, J=7.5 Hz); 7.39 (br.d, 1H, J=8.1 Hz); 7.41 (br.d, 1H; J=7.6 Hz); 7.48 (dt, 1H, J$_1$=7.6 Hz, J$_2$=1.3 Hz); 7.57 (t, 1H, J=7.7 Hz); 7.57 (s, 1H); 7.70-7.75 (m, 2H); 7.88 (t, 1H, J=1.5 Hz); 7.97 (br.d, 1H, J=7.8 Hz).

EXAMPLE 5

(5-{2-[(4',5'-Dihydroxy-2'-nitro-biphenyl-3-carbonyl)-amino]-phenyl}-thiophen-2-yl)-acetic acid (118)

SCHEME 21

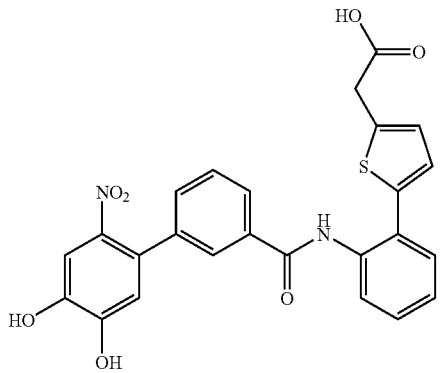

118

(5-{2-[(4',5'-Dihydroxy-2'-nitro-biphenyl-3-carbonyl)-amino]-phenyl}-thiophen-2-yl)-acetic acid (118) is made starting from amine (87) and carboxylic acid chloride (95) according to the procedure described above in steps 1 to 3 of EXAMPLE 3 to obtain (5-{2-[(4',5'-Dihydroxy-2'-nitro-biphenyl-3-carbonyl)-amino]-phenyl}-thiophen-2-yl)-acetic acid (118) (14 mg, 29% over 3 steps) as a yellow solid. $^1$H NMR (400 MHz, CD$_3$OD): 3.85 (s, 2H); 6.83 (s, 1H); 6.97 (d, 1H, J=3.5 Hz); 7.17 (d, 1H, J=3.5 Hz); 7.37 (td, 1H, J$_1$=7.6 Hz, J$_2$=1.5 Hz) 7.43 (td, 1H, J$_1$=7.6 Hz, J$_2$=1.8 Hz); 7.47 (br.d, 1H, J=7.6 Hz); 7.55 (t, 1H, J=7.6 Hz), 7.56 (s, 1H), 7.64 (dd, 1H, J$_1$=7.3 Hz, J$_2$=1.0 Hz); 7.69 (d, 1H, J=7.6 Hz); 7.83 (br.s, 1H); 7.93 (br.d, 1H, J=7.6 Hz).

EXAMPLE 6

5-{2-[(4',5'-Dihydroxy-2'-nitro-biphenyl-3-carbonyl)-amino]-phenyl}-thiophene-2-carboxylic acid (119)

SCHEME 22

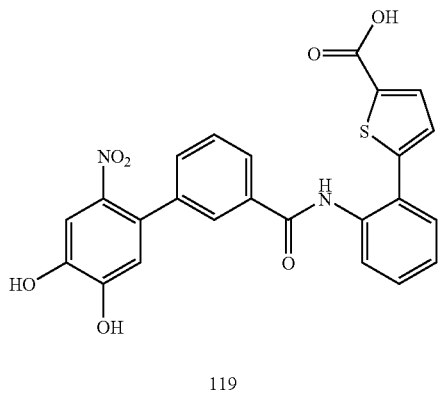

119

5-{2-[(4',5'-Dihydroxy-2'-nitro-biphenyl-3-carbonyl)-amino]-phenyl}-thiophene-2-carboxylic acid (119) is made starting from amine (90) and carboxylic acid chloride (95) according to the procedure described above in steps 1 and 3 of EXAMPLE 3 to obtain 5-{2-[(4',5'-Dihydroxy-2'-nitro-biphenyl-3-carbonyl)-amino]-phenyl}-thiophene-2-carboxylic acid (119) (6 mg, 8% over 2 steps) as a yellow solid. $^1$H NMR (400 MHz, CD$_3$OD): 6.84 (s, 1H); 7.35 (d, 1H, J=3.8 Hz); 7.41-7.63 (m, 6H); 7.71 (dd, 1H, J$_1$=7.8 Hz, J$_2$=1.3 Hz); 7.75 (d, 1H, J=3.8 Hz); 7.86 (br.s, 1H); 7.93 (br.d, 1H, J=7.6 Hz).

EXAMPLE 7

5-{2-[(2'-3'-Dihydroxy-5'-nitro-biphenyl-3-carbonyl)-amino]-phenyl}-thiophene-2-carboxylic acid (120)

SCHEME 23

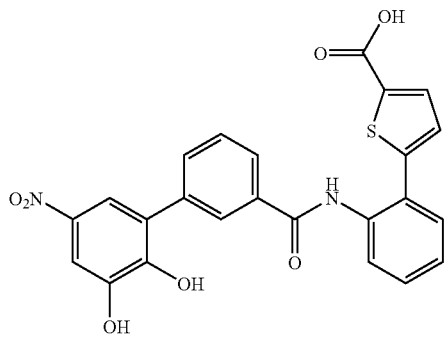

120

5-{2-[(2'-3'-Dihydroxy-5'-nitro-biphenyl-3-carbonyl)-amino]-phenyl}-thiophene-2-carboxylic acid (120) is made starting from amine (90) and carboxylic acid chloride (99) according to the procedure described above in steps 1 to 3 of EXAMPLE 3 to obtain 5-{2-[(2'-3'-Dihydroxy-5'-nitro-biphenyl-3-carbonyl)-amino]-phenyl}-thiophene-2-carboxylic acid (120) (17 mg, 15% over 3 steps) as a yellow solid. $^1$H NMR (400 MHz, CD$_3$OD): 7.36 (d, 1H, J=4.0 Hz); 7.44 (td, 1H, J$_1$=7.6 Hz, J$_2$=1.5 Hz); 7.51 (td, 1H, J$_1$=7.6 Hz, J$_2$=1.5 Hz); 7.59-7.67 (m, 2H); 7.69-7.75 (m, 3H); 7.86-7.97 (m, 3H); 8.21 (br.s, 1H).

EXAMPLE 8

(5-{2-[2-(3,4-Dihydroxy-5-nitro-phenyl)-acetylamino]-phenyl}-thiophen-2-yl)-acetic acid (121)

SCHEME 24

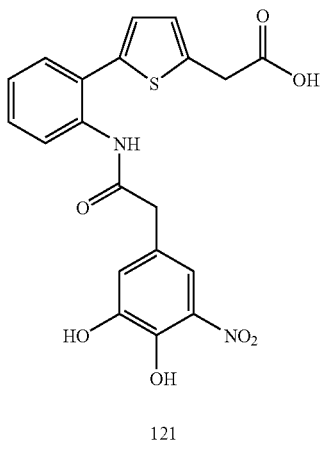

121

(5-{2-[2-(3,4-Dihydroxy-5-nitro-phenyl)-acetylamino]-phenyl}-thiophen-2-yl)-acetic acid (121) is made starting from amine (87) and carboxylic acid chloride (107) according to the procedure described above in steps 1 to 3 of EXAMPLE 1 to obtain (5-{2-[2-(3,4-Dihydroxy-5-nitro-phenyl)-acetylamino]-phenyl}-thiophen-2-yl)-acetic acid (121) (8 mg, 10% over 3 steps) as a yellow solid. $^1$H NMR (400 MHz, CD$_3$OD): 3.65 (s, 2H); 3.81 (s, 2H); 6.83-6.89 (m, 2H); 7.17 (br.s, 1H); 7.27 (td, 1H, J$_1$=7.6 Hz, J$_2$=1.5 Hz); 7.36 (td, 1H, J$_1$=7.7 Hz, J$_2$=1.5 Hz); 7.48 (dd, 1H, J$_1$=7.8 Hz, J$_2$=1.5 Hz); 7.55 (s, 1H); 7.69 (br.d, 1H, J=8.1 Hz).

Results from sLe$^x$TSA: IC$_{50}$ Data for E-/P-/L-Selectin

| Compound | IC$_{50}$ E-Selectin [μM] | IC$_{50}$ P-Selectin [μM] | IC$_{50}$ L-Selectin [μM] |
|---|---|---|---|
| 116 | 308.3 | 5.2 | 8.7 |
| 118 | — | 19.2 | 39.2 |
| 119 | 272.0 | 11.0 | 17.1 |
| 120 | — | 4.6 | 6.6 |

Data from Flow Chamber Assay for E- and P-Selectin

Values are given as normalized ratios of %-inhibition of compound x divided by %-inhibition of bimosiamose.

| Compound | E-Selectin [Ratio] | P-Selectin [Ratio] |
|---|---|---|
| 110 | 1.00 | 1.26 |
| 113 | 1.37 | 1.30 |
| 116 | 1.23 | 1.32 |
| 117 | n.s. | 0.83 |
| 118 | 0.84 | 1.19 |
| 119 | 0.86 | 1.67 |
| 120 | 1.01 | 1.72 |
| 121 | 0.98 | 0.89 |

The compounds referred to in the following SCHEME 10 are those compounds referred to as the particularly preferred compounds herein.

SCHEME 10

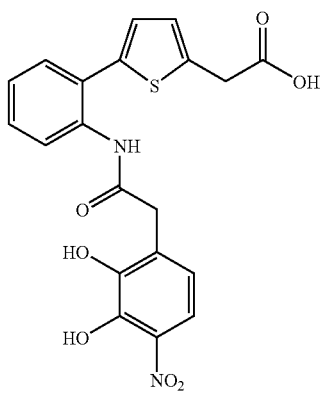

42

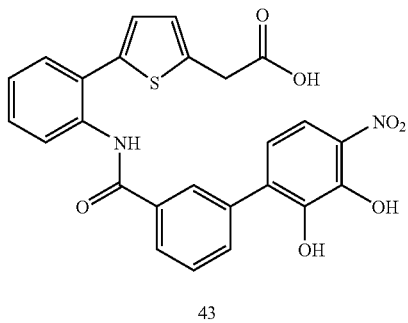

43

-continued
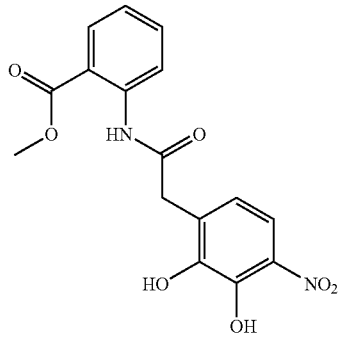
44
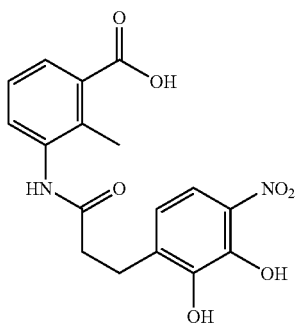
45
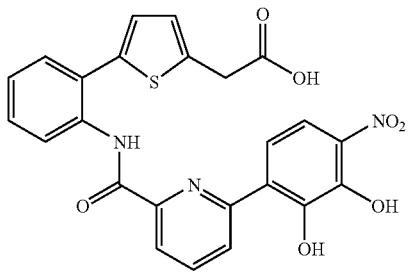
46
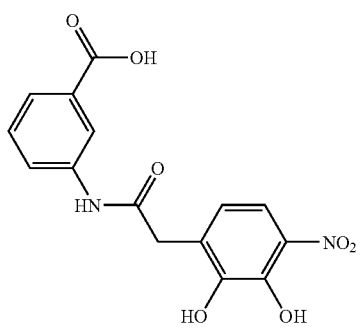
47
-continued
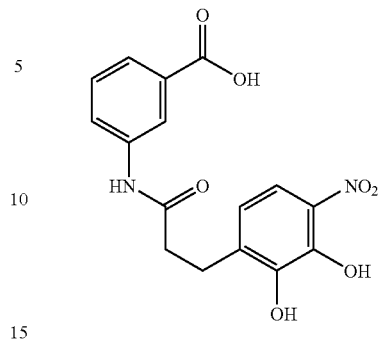
48
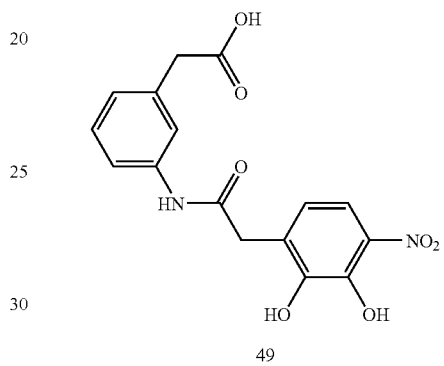
49
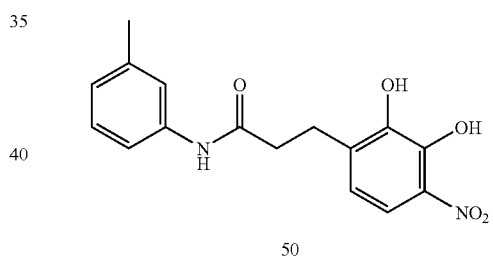
50
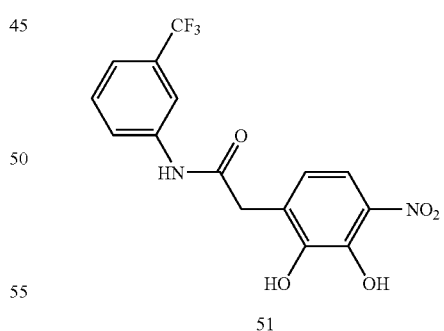
51
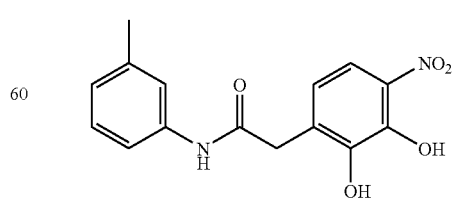
52

-continued
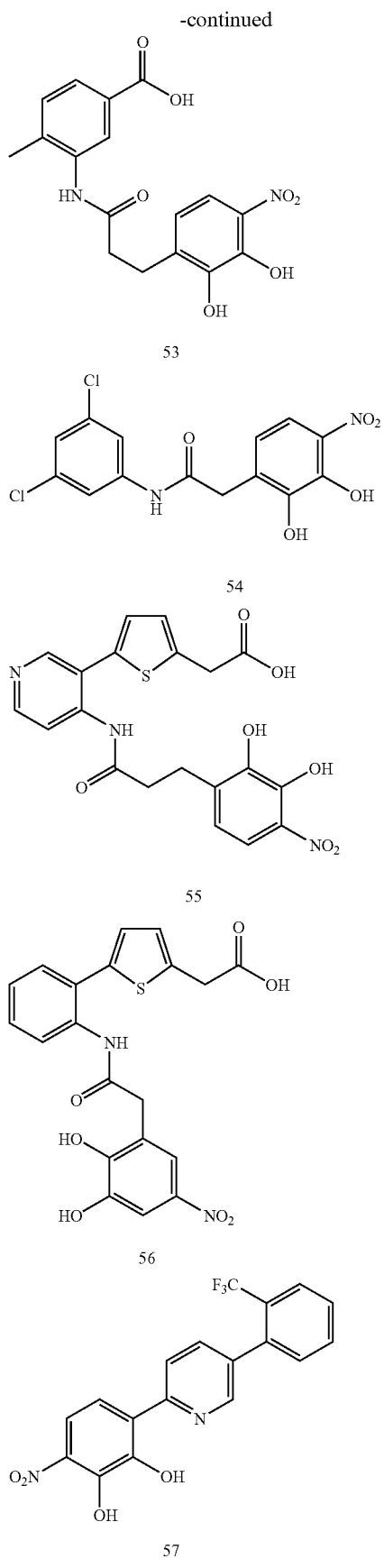
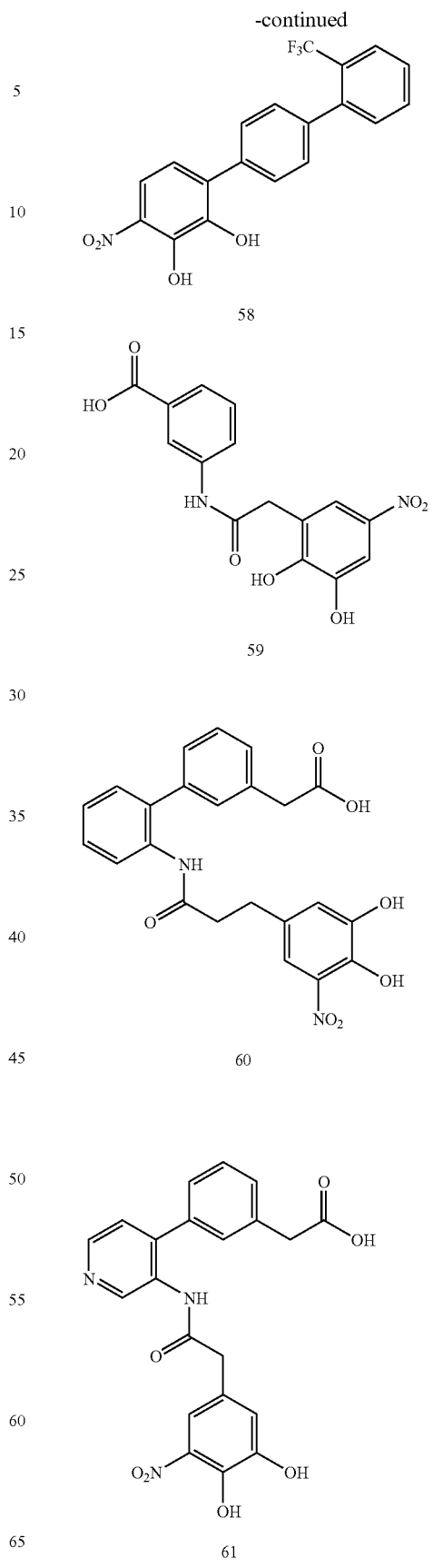

-continued
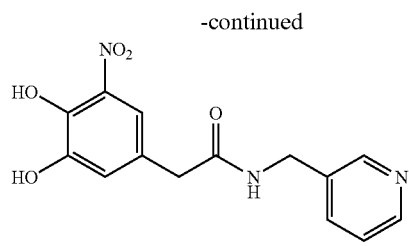
62
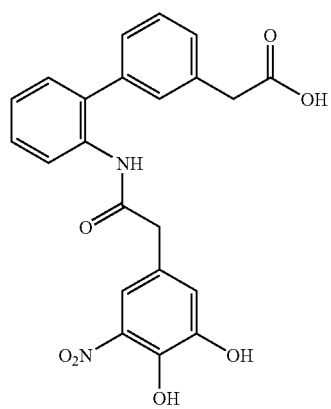
63
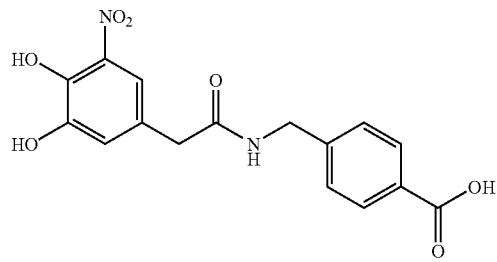
64
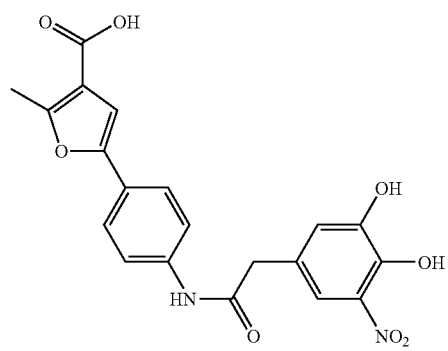
65
-continued
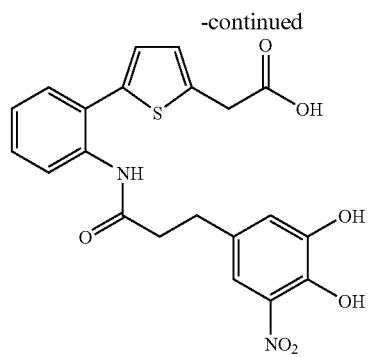
66
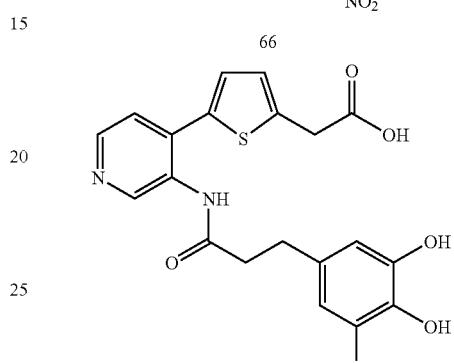
67
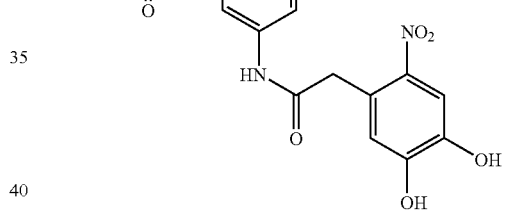
68
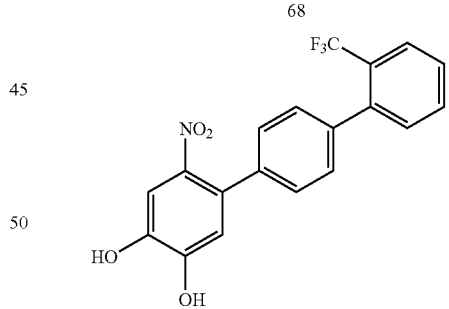
69
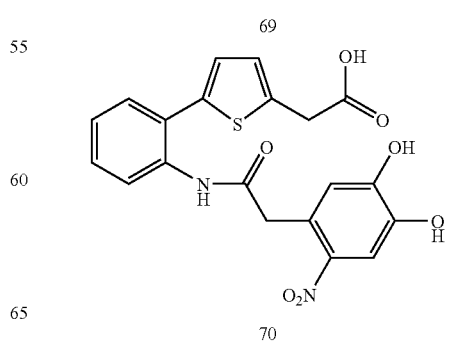
70

-continued
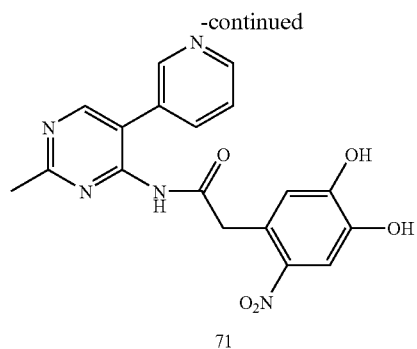
71
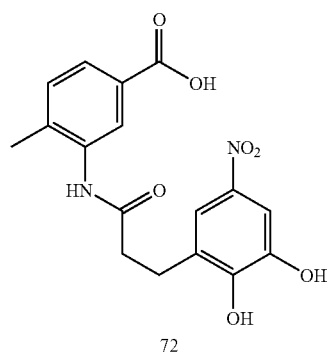
72
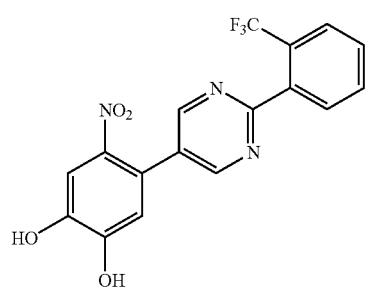
73
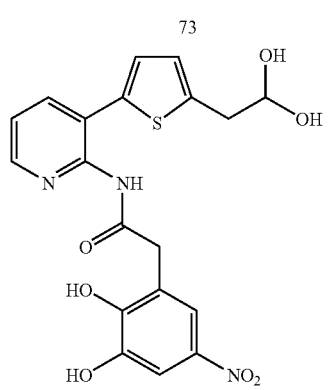
74
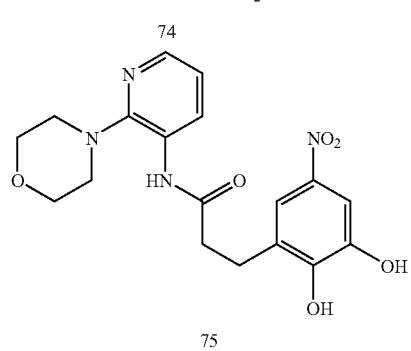
75
-continued
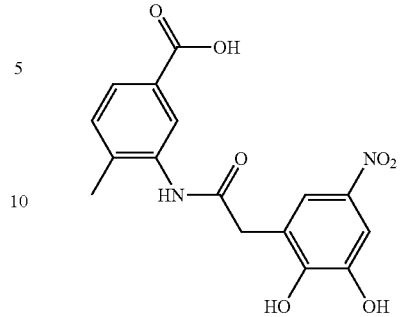
76
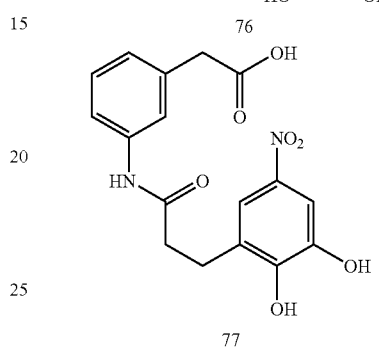
77
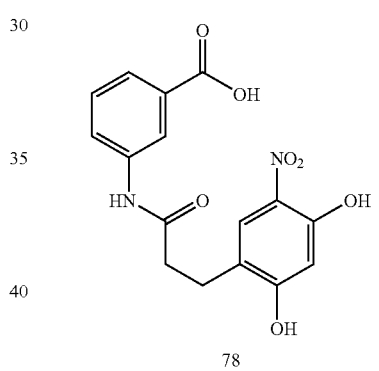
78
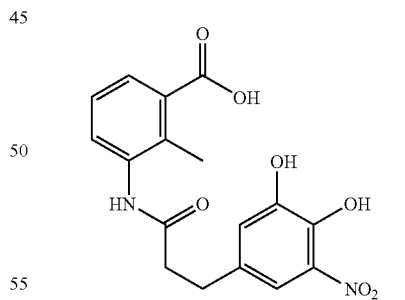
79
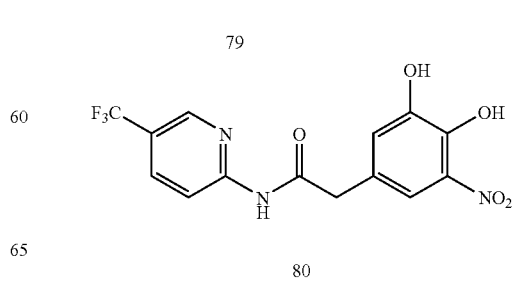
80

-continued

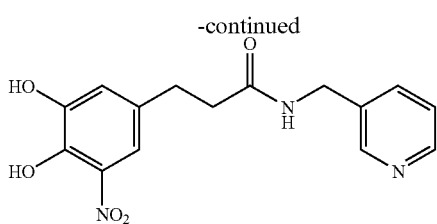
81

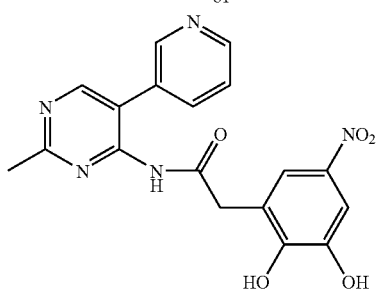
82

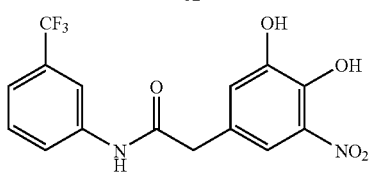
83

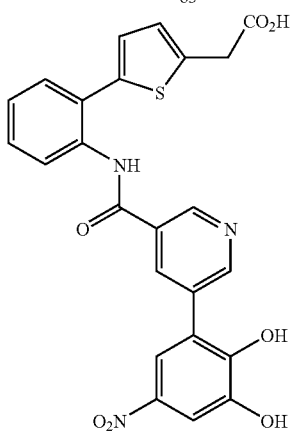
84

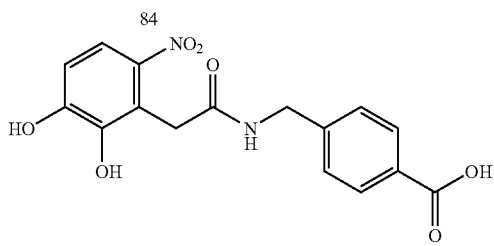
85

Sialyl Lewis$^x$ Tyrosine Sulfate Assay (sLe$^x$ TSA):

Compounds of the present invention are assayed on a molecular level for their ability to inhibit the binding of P-, L-, or E-selectin chimeric molecules to sLe$^x$ and tyrosinesulfate residues linked to a polymeric matrix as a PSGL-1 substitute. Selected IC$_{50}$-values are determined.

Microtiter plates are coated overnight in carbonate buffer pH9.6 with goat anti human Fc mAB (10 µg/ml). After washing in assay buffer (25 mM 4-(2-hydroxyethyl)-1-piperazineethanesulfonic acid (HEPES), 150 mM NaCl, 1 mM CaCl$_2$, pH7.4) and blocking (3% bovine serum albumin (BSA) in assay buffer) plates are incubated for 2 h at 37° C. with human P-Selectin-IgG-chimera (0.61 nM respectively 150 ng/mL) or human L-Selectin-IgG-chimera (0.61 nM respectively 89 ng/mL) or human E-Selectin-IgG-chimera (0.61 nM respectively 131 ng/mL). 5 µl of sLe$^x$-tyrosine sulfate polyacrylamide (1 mg/ml) carrying 15% sLe$^x$, 10% Tyrosine-sulfate and 5% biotin is complexed with 2011 Streptavidin-Peroxidase solution (1 mg/ml) and 25 µl assay buffer without CaCl$_2$. For use in the assay, the ligand complex is diluted 1:10000 in assay buffer and further diluted 1:1 with varying amounts of compounds in assay buffer incl. 2% DMSO. This mixture is added to the wells precoated with E- or P-selectin. After incubation for 2 h at 37° C., wells are washed for six times with in assay buffer incl. 0.005% Polyoxyethylenesorbitan monolaurate (TWEEN 20), developed for 10-15 min with 20 µl 3,3',5,5'-tetramethylbenzidine (TMB)/H$_2$O$_2$ substrate solution and stopped with 20 µl 1M H$_2$SO$_4$. Bound sLe$^x$-Tyrosine sulfate ligand complex is determined by measuring optical density at 450 nm vs. 620 nm in a Fusion alpha-FP reader (sold from Packard Bioscience, Dreieich, Germany).

Flow Chamber Assay/Cell Adhesion and Rolling Under Flow Conditions

To assess the capability of compounds to inhibit cell binding under dynamic conditions resembling the flow in a blood vessel, flow chamber assays addressing/testing binding of HL-60 cells/various cell lines to P-selectin, L-selectin and E-selectin chimeric molecules are performed.

Cell attachment under flow conditions are determined using a parallel flow chamber system. A 35 mm polystyrene culture dish is coated for 1 hour at room temperature with coating buffer (50 mM tris-(hydroxymethyl)aminomethane buffer (Tris), 150 mM NaCl, 2 mM CaCl$_2$; pH 7.4) containing human E- or P-selectin-IgG chimera at concentrations of 2.5 µg/ml or 10 µg/ml, respectively. After removal of the coating solution non specific binding sites are blocked for an additional hour with 1% BSA in coating buffer at room temperature. After washing with assay buffer ("Roswell Park Memorial Institute 1640" (RPMI 1640)+10 mM HEPES) the dish is fitted into a parallel plate laminar flow chamber (sold from Glycotech, Rockville, Md.) and mounted on an inverted phase-contrast microscope (sold from Olympus, Hamburg, Germany) equipped with a CCD camera (JVC) that is connected to a PC. Employing a peristaltic pump (sold from Ismatec, Wertheim-Mondfeld, Germany) the re-circulating system is equilibrated with assay buffer containing 125 µM compound or vehicle control (DMSO). Cells (1 million/ml) are added to the chamber and allowed to distribute for 2 minutes at a high flow rate. The flow rate is then decreased resulting in a calculated flow shear of 1 dyne/cm$^2$. Video sequences of 10 low power fields are digitally recorded after 5 minutes continuous flow. The percentage of inhibition is calculated from the mean number of cells per field that attached to the coated dish surface in the presence versus absence of compound of at independent experiments.

The invention claimed is:

1. A chemical compound of the formula (IIb) or (IIc) or (IIe) or (IIf):

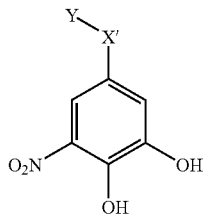
IIb

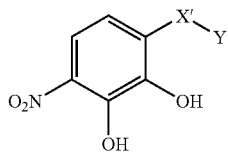
IIc

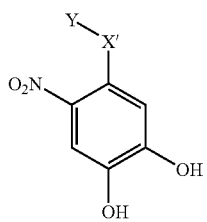
IIe

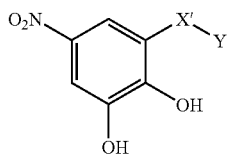
IIf wherein:
X' is

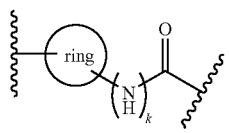
(b)

in which "ring" is

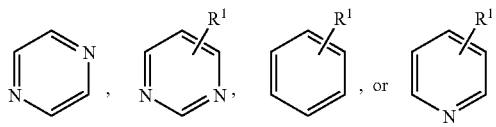

$R^1$ is H, $NO_2$, $CF_3$, F, Cl, Br, I, CN, $CH_3$, $NH_2$, NHAlkyl, NHAryl, or NHAcyl; and k is 0 or 1, Y is

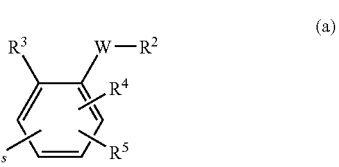
(a)

in which s is 0 or 1,
$R^2$ is $CO_2H$, $CO_2$Alkyl, $CO_2$Aryl, $CO_2NH_2$, $CO_2$Aralkyl, $SO_3H$, $SO_2NH_2$, $PO(OH)_2$, 1-H-tetrazolyl-, CHO, $COCH_3$, $CH_2OH$, $NH_2$, NHAlkyl, N(Alkyl)Alkyl', $OCH_3$, $CH_2OCH_3$, SH, F, Cl, Br, I, $CH_3$, $CH_2CH_3$, CN, or $CF_3$;
$R^3$ independently from $R^2$ is H, $CH_3$, $CH_2CH_3$, $CF_3$, F, Cl, Br, I, CN, or $NO_2$;
$R^4$ independently from $R^2$ and $R^3$ is H, $CH_3$, $CH_2CH_3$, $CF_3$, F, Cl, Br, I, CN, $NO_2$, or $R^2$;
$R^5$ is H, $NO_2$, $CF_3$, F, Cl, Br, I, CN, $CH_3$, $OCH_3$, SH, or $NH_2$;
W is —$(CH_2—)_v$, cis-CH=CH— or trans-CH=CH—, and v is 0, 1, or 2;
in case that —W— is cis-CH=CH— or trans-CH=CH—, $R^2$ must not be $NH_2$ or SH;

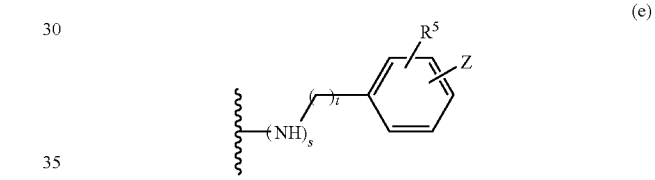
(e)

in which t is 0, 1, or 2;

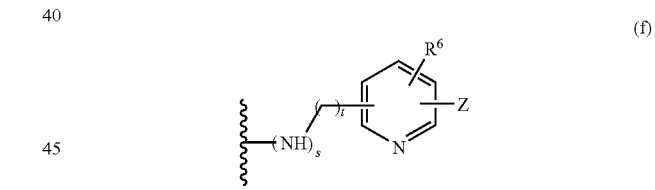
(f)

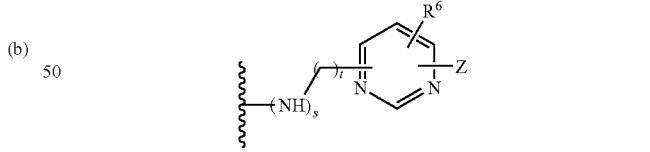
(g)

$R^6$ independently from $R^2$ is H, F, Cl, Me, tert-Bu, CN, or $NH_2$;
Z is

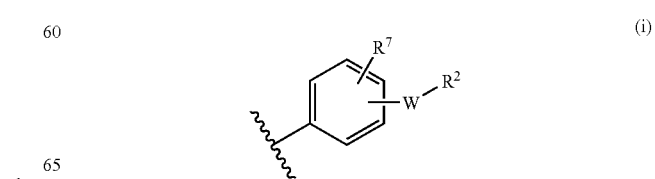
(i)

$R^7$ independently from $R^2$ is H, $NO_2$, $CF_3$, F, Cl, Br, I, CN, $CH_3$, $OCH_3$, SH, or $NH_2$;

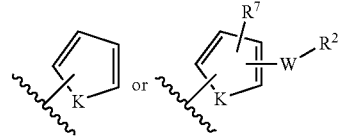
(iv)

in which K is NH, NMe, O, or S;

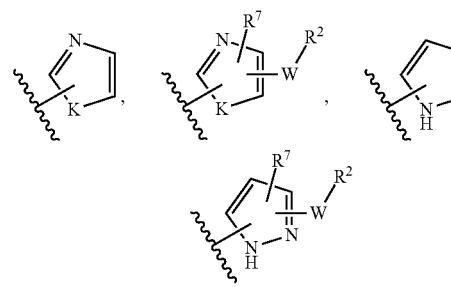
(v)

or a pharmaceutically acceptable salt, ester or amide thereof and of the above identified compounds of formula (IIb) or (IIc) or (IIe) or (IIf).

2. The chemical compound of claim 1 defined by formula (A2) or (A3) or (A5) or (A6) or (B2) or (B3) or (B5) or (B6)

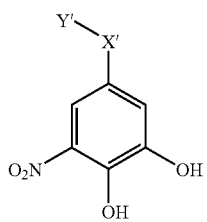
A2

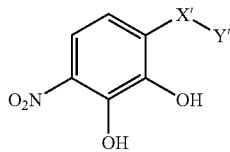
A3

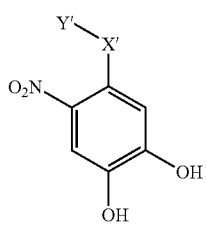
A5

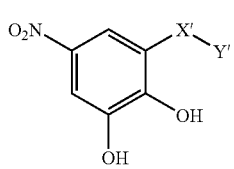
A6

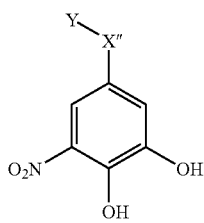
B2

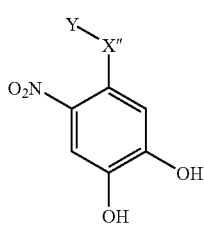
B3

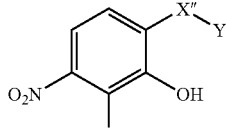
B5

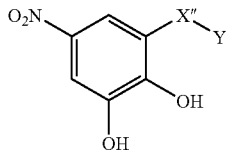
B6 wherein X' and Y are as defined in claim 1 and wherein X'' is

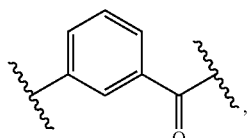 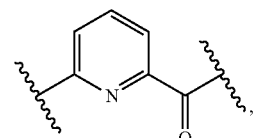

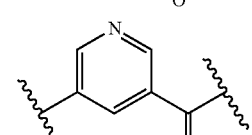 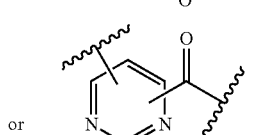

 or 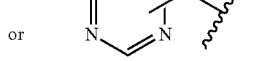

and wherein —Y' is

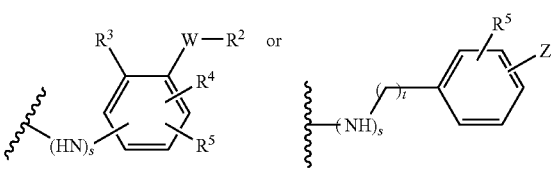

wherein all indices, symbols, and substituents are as defined in claim 1.

3. The chemical compound of claim 1, defined by the formula (C2) or (C3) or (C5) or (C6):
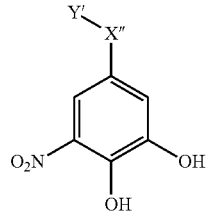 C2
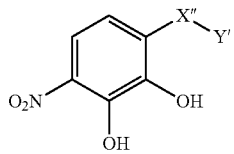 C3
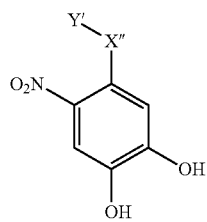 C5
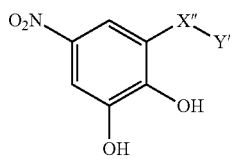 C6
wherein X" is
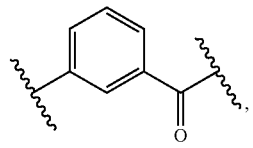 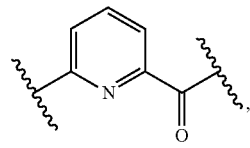
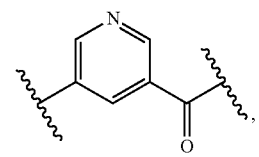, or 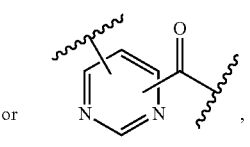,
and wherein Y' is
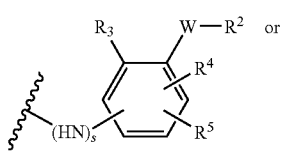 or
-continued
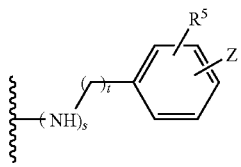
wherein all indices, symbols, and substituents are as defined in claim 1.
4. The chemical compound of claim 1 defined by formula (D2) or (D3) or (D5) or (D6):
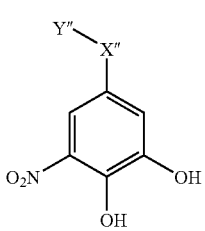 D2
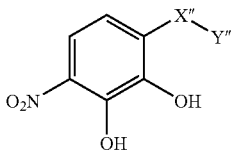 D3
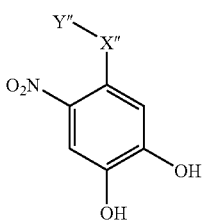 D5
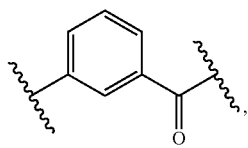 D6
wherein X" is
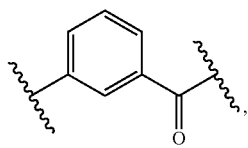 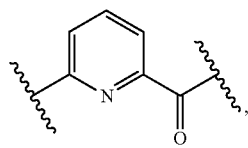
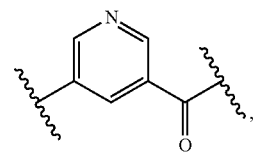, or 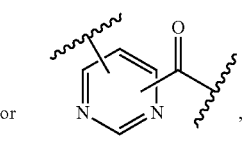, and Y" is

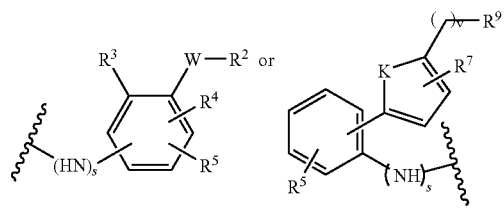

wherein $R^9$ is $CO_2H$, $CO_2$alkyl, $CO_2$aryl, $CO_2NH_2$, $CO_2$aralkyl, 1-H-tetrazolyl, CHO, COCH3, $CH_2OH$, or $CH_2OCH_3$, wherein all indices, symbols, and substituents are as defined in claim 1.

5. A pharmaceutical composition comprising at least one chemical compound of claim 1 and a pharmaceutically acceptable excipient.

6. A pharmaceutical composition comprising at least one chemical compound of claim 2 and a pharmaceutically acceptable excipient.

7. A pharmaceutical composition comprising at least one chemical compound of claim 3 and a pharmaceutically acceptable excipient.

8. A pharmaceutical composition comprising at least one chemical compound of claim 4 and a pharmaceutically acceptable excipient.

9. A cosmetic or dermatological composition, comprising at least one chemical compound having the structure of formula (IIb) or (IIc) or (IIe) or (IIf) as defined in claim 1.

10. A cosmetic composition comprising at least one chemical compound of the formula (IIb) or (IIc) or (IIe) or (IIf) as in claim 1 and at least one cosmetically tolerable component.

11. A dermatological composition comprising at least one chemical compound of formula (IIb) or (IIc) or (IIe) or (IIf) as in claim 1 and at least one dermatologically tolerable component.

12. A method of treating inflammation, comprising the administration of a therapeutic amount of at least one chemical compound having the structure of formula (IIb) or (IIc) or (IIe) or (IIf) as defined in claim 1.

\* \* \* \* \*